United States Patent [19]

Levenson et al.

[11] Patent Number: 4,751,313
[45] Date of Patent: Jun. 14, 1988

[54] PRECURSOR TO NUCLEIC ACID PROBE

[75] Inventors: Corey H. Levenson, Oakland; Kary B. Mullis, Kensington, both of Calif.

[73] Assignee: Cetus Corporation, Emeryville, Calif.

[21] Appl. No.: 72,531

[22] Filed: Jul. 13, 1987

Related U.S. Application Data

[60] Division of Ser. No. 888,252, Jul. 21, 1986, Pat. No. 4,705,886, and Ser. No. 791,332, Oct. 25, 1985, Pat. No. 4,617,261, which is a continuation-in-part of Ser. No. 683,263, Dec. 18, 1984, Pat. No. 4,582,789, which is a continuation-in-part of Ser. No. 591,811, Mar. 21, 1984, abandoned.

[51] Int. Cl.$^4$ ............................................ C07D 495/04
[52] U.S. Cl. .................................................... 548/303
[58] Field of Search ........................................ 548/303

[56] References Cited

U.S. PATENT DOCUMENTS

| | | | |
|---|---|---|---|
| 2,715,634 | 8/1955 | Weijlard et al. | 548/303 |
| 4,014,895 | 3/1977 | Aoki et al. | 548/303 |
| 4,124,598 | 11/1978 | Hearst et al. | 536/22 X |
| 4,582,789 | 4/1986 | Sheldon et al. | 435/6 |
| 4,617,261 | 10/1986 | Sheldon et al. | 435/6 |

FOREIGN PATENT DOCUMENTS 0063879  11/1982  European Pat. Off. ............... 536/22

OTHER PUBLICATIONS

W. Saffran et al., *Proc. Natl. Acad. Sci. USA*, 79, 4594–4598 (1982).
D. Schwartz et al., *CSH Laboratory Symposium* XLVII.

*Primary Examiner*—Richard A. Schwartz
*Attorney, Agent, or Firm*—Albert P. Halluin; Janet E. Hasak

[57] ABSTRACT

Nucleic acids may be labeled by intercalating the alkylating intercalation moiety of a labeling reagent into a partially double-stranded nucleic acid to form a complex and activating the complex to cause covalent bonding between the reagent and the nucleic acid. Preferably, the labeled nucleic acid is a hybridization probe for detecting nucleic acid sequences capable of hybridizing with a hybridizing region of the nucleic acid. Also preferably the label moiety is non-radioactive. The labeling reagent is of the formula:

[A][B]L where A is an alkylating intercalation moiety, B is a divalent organic moiety of the formula:

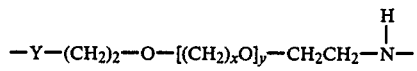

where Y is O, NH or N—CHO, x is a number from 1 to 4, y is a number from 2 to 4, and L is a monovalent label moiety, wherein B is exclusive of any portion of the intercalation and label moieties.

Preferably A is a 4-methylene-substituted psoralen moiety, and most preferably A is a 4′-methylene-substituted-4,5′,8-trimethylpsoralen moeity and L is biotin.

2 Claims, No Drawings

PRECURSOR TO NUCLEIC ACID PROBE

This is a division of application Ser. No. 888,252, filed July 21, 1986, now U.S. Pat. No. 4,705,886, which is a divisional application of U.S. Ser. No. 791,332 filed Oct. 25, 1985, now U.S. Pat. No. 4,617,261, which is a continuation-in-part application (CIP) of U.S. Ser. No. 683,263 filed Dec. 18, 1984, now U.S. Pat. No. 4,582,789, which is a CIP of U.S. Ser. No. 591,811 filed Mar. 21, 1984, now abandoned. This patent application is also related to copending U.S. application Ser. No. 791,323 filed Oct. 25, 1985.

BACKGROUND OF THE INVENTION

This invention relates to a means of labeling nucleic acids, preferably DNA. More particularly, this invention is directed to a process for preparing labeled nucleic acids by use of alkylating intercalators containing a label moiety, where the word label is intended to include moieties which may be detected both directly and indirectly. In addition, this invention relates to a means for detecting the presence of a nucleic acid sequence such as a gene using a hybridization probe containing a complementary nucleic acid sequence.

In biomedical research and recombinant DNA technology it is often useful to have indicator probes which allow the user to detect, monitor, localize or isolate nucleic acids when present in any amount. DNA hybridization probes, for example, contain a nucleic acid sequence complementary to the nucleic acid sequence or to the gene to be detected. Such probes have been used to detect the presence of genes coding for antigens responsible for graft rejection, such as human leukocyte antigens (HLA), or genetic disease, such as sickle cell anemia. For example, Sood et al., PNAS, 78, 616–620 (1981) describe the isolation of cDNA clones for HLA-B antigens. These clones were prepared by synthesizing cDNA from an mRNA mix containing mRNA coding for the desired HLA antigen, inserting the cDNA into a vector, transforming a bacterial host and isolating transformant clones that contain the desired DNA segment by probing with an oligonucleotide probe that is specific for the desired DNA sequence. Ploegh et al., PNAS, 77, 6081–6085 (1980) have also reported cloning a cDNA probe for an HLA gene sequence. In addition, U.S. Pat. No. 4,358,535 to Falkow et al. describe a method for detecting infectious disease-causing microbes using labeled nucleotide probes complementary to nucleic acid contained by the pathogenic microbe. Until recently, the materials most sensitive and therefore useful for this purpose were radioactively labeled nucleic acids such as those labeled with isotopes of, e.g., hydrogen ($^3$H), phosphorus ($^{32}$P) or iodine ($^{125}$I).

Brown et al., Gene, 20, 139–144 (1982) teaches stabilizing radioactive RNA-DNA hybridization probes using trimethylpsoralen.

Such radioactive compounds, however, suffer from various drawbacks, including extensive safety precautions, expensive equipment, health-monitoring services and waste treatment, and high usage costs due to the instability of the materials. Therefore, there is an increasing incentive to search for suitable nonradioactive labels for nucleic acids which would provide sensitive probes.

Already known is that haptens can initiate an immune response if bound to a carrier, so to be useful for labeling and identification. Thus, for example, hapten-labeled DNA can be detected with antibodies.

Methods have been developed using non-radioactive biotin-avidin complexes for visually localizing specific proteins, lipids or carbohydrates on or within cells and for labeling DNA. For example, Manning et al., Chromosoma, 53, 107 (1975) have determined the chromosomal location of ribosomal genes by electron microscopy using a biotinized protein, cytochrome C, chemically crosslinked to RNA as a hybridization probe. Langer et al., Proc. Natl. Acad. Sci. USA, 78, 6633–6637 (1981) describe a method for labeling DNA by enzymatic incorporation of nucleotide analogs containing functional groups such as biotin via DNA polymerase I, and Leary et al., Proc. Natl. Acad. Sci. USA, 80, 4045–4049 (1982) have used this method to label DNA probes with biotinylated nucleotides. Also, it is well known how to attach chemical moieties to pyrimidine and purine rings using an acetoxymercuration reaction whereby covalently bound mercury atoms are introduced into the 5-position of the pyrimidine ring, the C-8 position of the purine ring, or the C-7 position of a 7-deazapurine ring. European Patent Publication No. 0,063,879 to Ward et al. describes the preparation of a nucleotide derivative by a process where a mercurated intermediate is formed which reacts with a reactive chemical moiety which may be the label or which then reacts with the label compound. The derivative contains biotin, iminobiotin, lipoic acid or other label attached covalently to the pyrimidine or purine ring which will interact with proteins such as avidin or antibodies. When biotin is bound specifically by an avidin-linked enzyme complex, detection is seen as a color change in a chromogenic substrate. When an avidin-alkaline phosphatase complex is used to detect biotinylated DNA probes after hybridization, sensitivity has been shown to approach that of autoradiography used to detect $^{32}$P labeled probes. In this method, the labeled nucleotide is then enzymatically incoporated into DNA so that the DNA is labeled.

Methods also exist for studying the molecular structure of DNA. For example, psoralens, which are a class of planar furocoumarin molecules capable of intercalating into double-stranded DNA in the presence of single-stranded DNA, will covalently bond to and crosslink DNA when activated by long-wave (>350 nm) UV light. Covalent bonding involves a two-step process: (1) initial non-covalent binding of the planar-structured psoralen between the base pairs in the double helix structure of the nucleic acid to produce a psoralen-nucleic acid complex and (2) irradiation of the complex with light of the proper wavelength to form covalent bonds between the psoralen molecules and pyrimidine nucleotides which occur as integral entities of nucleic acid strands.

This covalent bonding enables the study in vivo of secondary structures of DNA such as packaging of nucleic acid within viruses. Use of 4'-adducts of 4,5',8-trimethylpsoralen to bond DNA covalently is described in U.S. Pat. No. 4,124,598 to Hearst et al. Hearst, Rapoport and others have extensively studied the incorporation of psoralens into DNA and RNA. Song et al., ANYAS (1980) 355–67 and Hyde et al., Biochemistry, 17 (1978) 1251–7 disclose use of psoralen compounds to study secondary structures.

Schwartz et al., CSH Laboratory Symposium XLVII discloses DNA crosslinkiing with DNA or proteins using various psoralen containing compounds. Saffran et al., *Proc. Natl. Acad. Sci. U.S.A.*, 79, 4594–4598 (1982) describes use of one of these compounds containing a thiol group for site-directed psoralen crosslinking of DNA to enable structural analysis of DNA. In this process the plasmid DNA molecule has mercurated nucleotides incorporated near a restriction site so that the psoralen is directed to the bases through a Hg-S linkage. Use of mercurated compounds in reaction synthesis involves extra expense and necessitates safety precautions in view of the toxicity of mercury.

U.S. patent application Ser. No. 444,438 filed Nov. 24, 1982 to Letsinger et al. describes bifunctional intercalators containing a phenanthridium moiety as an agent for introducing markers (e.g., fluorescent probes) at specified regions in polynucleotides, presumably for determining secondary structure.

In addition to their use in studying nucleic acid secondary structure, commercial applications of the psoralen derivatives include their use in treating certain dermatological disorders and for viral inactivation to produce vaccine.

Another use for compounds which label DNA is in chromosome banding or staining. An example described in the literature is the use of the Giemsa reagent to stain regions or bands of chromosomes differentially, as described in the article by V. G. Dev et al., *Lancet* (England) 1, 1285 (June 10, 1972). Because chromosomes have characteristic banding patterns, this procedure can be used to distinguish chromosomes. This ability to distinguish chromosomes has been very useful in the study of chromosome anomalies. For example, Down's syndrome can be diagnosed by determining that the individual is trisomic for chromosome 21.

SUMMARY OF THE INVENTION

To obviate the disadvantages associated with the labeled probes presently existing, the present invention provides a means for producing stable labeled nucleic acid hybridization probes which, rather than strong mercurated intermediates or enzymes, employs specific labeling compounds capable of both non-covalent binding and alkylation to introduce label moieties into nucleic acids.

As a further advantage the method herein is preferably employed to label nucleic acids nonradioactively to avoid the disadvantages of radioactive labeling.

Specifically, the invention herein relates to a process for labeling a partially double-stranded nucleic acid which comprises the steps of:

(a) contacting the nucleic acid with one or more labeling compositions of the formula:

[A]–[B]–L wherein A is an alkylating intercalation moiety, B is a divalent organic moiety having the formula:

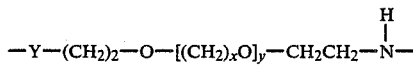

where Y is O, NH or N—CHO, x is a number from 1 to 4 and y is a number from 2 to 4, and L is a monovalent label moiety, wherein B is exclusive of any portion of the intercalation and label moieties, said contacting occurring so as to cause the alkylating intercalation moiety of the labeling composition to intercalate into the nucleic acid to form a complex; and (b) activating the complex so as to induce the alkylating intercalation moiety to bond covalently to at least one of the nucleic acid strands.

Preferably the alkylating intercalation moiety is 4'-methylene-substituted psoralen.

In another aspect, the invention relates to a process for preparing a labeled nucleic acid hybridization probe for detecting nucleic acid sequences which process comprises the steps of:

(a) contacting a nucleic acid comprising a double-stranded nucleic acid region adjacent to a single-stranded region capable of hybridization with the nucleic acid sequence to be detected, with at least one of the labeling compositions described above, said contacting causing the alkylating intercalation moiety of the labeling composition(s) to intercalate into the nucleic acid to form a complex; and (b) activating the complex to induce the alkylating intercalation moiety to bond covalently to the double-stranded nucleic acid region, via either one or both of the nucleic acid strands.

In still another aspect the invention relates to a process for preparing a labeled DNA hybridization probe for detecting DNA sequences which process comprises the steps of:

(a) inserting a DNA fragment which contains a sequence complementary to the sequence to be detected into the bacteriophage M13 genome at a restriction site therein and preparing therefrom circular single-stranded DNA containing the DNA fragment;

(b) cleaving double-stranded M13 DNA at a restriction site which is less than 100 base pairs from, or is the same as, the restriction site used to insert the DNA fragment in step (a);

(c) denaturing the cleaved double-stranded M13 DNA;

(d) hybridizing the circular single-stranded M13 phage isolated from step (a) with the denatured double-stranded M13 DNA;

(e) removing any single-stranded DNA from the mixture to obtain a circular partially double-stranded DNA;

(f) contacting the DNA from step (e) with at least one labeling composition described above, said contacting causing the alkylating intercalation moiety of the labeling composition(s) to intercalate into the DNA to form a complex; and (g) activating the complex to induce the alkylating intercalation moiety to bond covalently to the double-stranded DNA region, via either one or both of the DNA strands.

Preferably these processes are carried out using non-radioactively labeled reagents.

The invention also includes the hybridization probe itself comprising a nucleic acid which comprises the single-stranded region described above, where the nucleic acid is covalently bound to one or more alkylating intercalation moieties and where the alkylating intercalation moiety is bound to the spacer arm which is in turn bound to the label moiety. The spacer arm is of the formula:

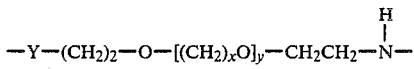

where Y is O or NH or N—CHO, x is a number from 1 to 4, and y is a number from 2 to 4. Preferably the probe is a double-stranded circular nucleic acid with a single-stranded insert.

In a further aspect the invention provides a process for detecting the probe comprising exposing the probe after hybridization to a means by which the label moiety of the probe is capable of being identified, and identifying the label moiety using an appropriate identification technique. Examples of such techniques include spectroscopic, radioisotopic, photochemical, chemical, immunochemical or biochemical means as by using a polypeptide, lectin or antibody capable of forming a complex with the label moiety of the probe. Using the preferred biochemical means, the probe is contacted with a polypeptide, lectin or antibody capable of forming a complex therewith under suitable conditions so as to form the complex, said polypeptide, lectin or antibody being capable of or including a label which can be detected when the complex is formed, and the complex is detected using an appropriate detection technique.

In yet another embodiment of the invention, one or more nucleic acid sequences, preferably those characteristic of a pathogenic microbe or associated with HLA typing or a genetic disease, are detected by a process comprising:

(a) contacting a sample containing the nucleic acid(s) to be detected (which sample generally consists of cells, body fluid or viral or tissue sample) with an effective amount of reagent sufficient to expose the nucleic acids in the sample (e.g., to open the cells, body fluid, viral capsids, or tissue of the sample) and to separate the strands of the nucleic acid(s);

(b) depositing the sample before, during, or after step (a) on an inert support;

(c) contacting the deposited sample with an effective amount of reagent sufficient to affix a substantially single-stranded form of an nucleic acid(s) on the support;

(d) contacting the affixed nucleic acid single-stranded form with an effective amount of the hybridization probe as described above under hybridization conditions; and (e) detecting hybridization of the single-stranded nucleic acid sequences by means of the label moiety on the probe.

BRIEF DESCRIPTION OF THE DRAWINGS

FIG. 1 represents a restriction map of pCHL2 *Chlamydia trachomatis* plasmid cloned into the BamHI site of pBR322. The M13mp9CHL2.1 subclone of pCHL2 is an approximately 1500 base pair insert between the XmaI and PstI restriction sites as indicated.

FIG. 2 represents a restriction map of M13mp9CHL2.1 containing the insert from the plasmid pCHL2.

FIG. 3 represents the cloning region of M13mp9 (FIG. 3A) and the cloning region of M13mp10 (FIG. 3B).

DESCRIPTION OF THE PREFERRED EMBODIMENTS

The following terms as used in the specification and claims have the following definitions:

"Spacer arm" refers to a divalent organic moiety which is chemically non-reactive with the alkylating intercalation moiety and label moiety employed herein and contains no portion of either and is of the formula:

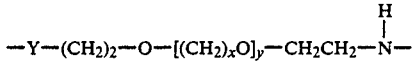

where Y is O, NH or N—CHO, x is 1 to 4 and y is 2 to 4. Preferably Y is O or NH, x is 2 and y is 2. The purpose of the spacer arm is to provide a chemical linkage between the alkylating intercalation moiety and the label moiety so that the label can readily interact with such detection means as antibodies, other detector polypeptides, or chemical reagents without interference. The number of atoms in the straight (main) chain of the spacer arm generally depends on the particular label moiety employed. The chain must be sufficiently long to permit access of the detector molecule to the binding site, i.e., to avoid interference by the nucleic acid. The molecular weight limits of the spacer arm (the values of x and y) will be determined by the types of atoms contained therein and by solubility considerations. As the molecular weight of, for example, polyethylene glycol increases, the spacer arm derived therefrom becomes less water soluble at room temperature and becomes more waxy. Thus, it is less useful in the present invention. The maximum molecular weight for the spacer arm is generally about 1000 to ensure adequate water solubility and fluidity thereof.

"Label moiety" refers to a monovalent moiety which is capable of producing a detectable signal, i.e., which can be detected in small quantities by detection means which generate a signal. Examples of suitable such means include spectroscopic or photochemical means, e.g., fluorescence or luminescence, or biochemical, immunochemical, or chemical means such as changes in physical, biochemical, immunochemical or chemical properties on contact with a detector analysis compound or reaction with a polypeptide or polypeptide/enzyme mixture to form a detectable complex. Thus, as used herein the term "label" is intended to include both moieties that may be detected directly, such as radioisotopes or fluorochromes, and reactive moieties that are detected indirectly via a reaction which forms a detectable product, such as enzymes that are reacted with substrate to form a product that may be detected spectrophotometrically. It is noted that the labeling reagent may contain a radioactive label moiety such as a radioisotope, but the preferred hybridization probe herein is nonradioactively labeled to avoid the disadvantages associated with radioactivity analysis.

"Body fluid" refers to fluid derived from a human or animal body or from a plant, such as, e.g., blood serum, cerebrospinal fluid, amniotic fluid, urine, and the like.

"Tissue" refers to biological tissue extract material which is not necessarily cellular by definition.

"Intercalation" (and "intercalate") as used herein refers to the initial non-covalent binding of the labeling composition herein between the base pairs in the nucleic acid double helix structure. The word does not imply that intercalation must necessarily occur, only that non-covalent binding, which includes both alkylation and intercalation, occurs. "Alkylating intercalation moiety" refers to moieties which initially intercalate with the nucleic acid and upon activation covalently bond to one or both of the nucleic acid strands. The preferred compounds are those which will irreversibly crosslink double-stranded nucleic acids, i.e., bond to both of the nucleic acid strands.

Examples of suitable alkylating intercalation compounds from which the moieties are derived include mitomycin C as described by Lown et al., *Can. J. Biochem.*, 54, 110ff (1976), carzinophilin A as described by Lown et al., *J.A.C.S.*, 104, 3213–3214 (1982), 3,5-diazido-5-ethyl-6-phenylphenanthridinium as described by Woolley et al., *Biochemistry*, 22, 3226–3231 (1983), psoralen compounds and derivatives thereof, and other compounds which can be devised which have structures allowing intercalation and alkylation, preferably irreversible crosslinking of nucleic acids, to occur. The preferred such moieties herein are 4'-methylene-substituted psoralen moieties such as those derived from psoralen compounds described and sold by HRI Associates, Inc., of Emeryville, Calif. via their Oct. 1, 1983 price schedule. These are preferred because their planar structure allows ready intercalation and they are able to crosslink the nucleic acids irreversibly. The 4'-methylene group is present to act as a link with the spacer arm. Examples of suitable psoralen moieties include 4'-methylene-substituted psoralen, 4'-methylene-substituted-5-methoxypsoralen, and 4'-methylene-substituted-4,5',8-trimethylpsoralen. The most preferred psoralen moiety herein is 4'-methylene-substituted-4,5',8-trimethylpsoralen due to its enhanced intercalating efficiency.

"Activation of the complex of alkylating intercalation moiety and nucleic acid" refers to means used to induce the alkylating intercalation moiety of the labeling reagent to bond covalently to the double-stranded region of the nucleic acid. The appropriate activation means will depend mainly on the type of alkylating intercalation moiety being employed. For example, the psoralen moieties and the moiety derived from 3,5-diazido-5-ethyl-6-phenylphenanthridinium will require activation by irradiation with ultraviolet light. Mitomycin C will form a complex activated by reduction thereof. Carzinophilin A will form a complex activated by protonation (acid activation) thereof. Thus, any means appropriate to the type of moiety employed for the reagent may be utilized for this purpose.

The label moiety of the labeling reagent herein is capable of producing a signal which can be detected by detection means. Examples of such detection means include spectroscopy, such as fluorescence and luminescence, photochemistry, radioactivity, biochemical means, immunochemical means, chemical means, and the like. Preferred means include forming a detectable complex with a polypeptide, lectin or antibody in the presence or absence of an enzyme associated with the polypeptide, lectin or antibody. Depending on the label moiety employed, an example of a polypeptide useful for this purpose is avidin or streptavidin complexed with an enzyme when biotin is the label moiety. Suitable antibodies would include, e.g., antibiotin antibodies or antidinitrophenol antibodies if the label moiety is dinitrophenol. Lectins, which are glycoproteins, would be employed as the detection means if carbohydrates are used as label moieties.

The detection means, if it is an antibody, a lectin, or some other polypeptide capable of complexing with the label moiety, would be linked to an entity capable of generating a detectable change. Examples of such entities include enzymes such as, e.g., alkaline phosphatase, which has chromogenic or fluorogenic substrates, or luciferase, which can generate luminescence. The label moiety may be any group possessing the detection properties described above, including haptens, which are only immunogenic when attached to a suitable carrier, but are capable of interacting with appropriate antibodies to produce detectable complexes.

Examples of suitable label moieties include those of the formula:

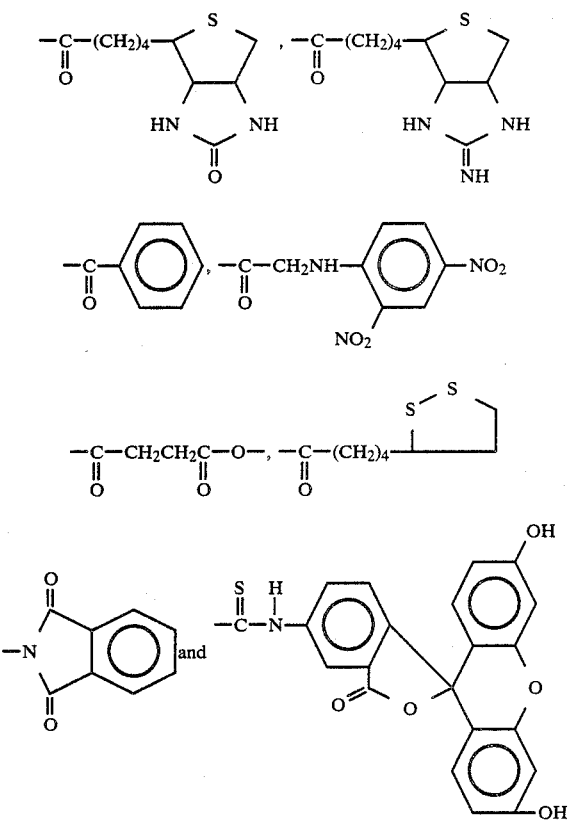

As label moieties containing aromatic groups tend to intercalate into the nucleic acid(s), the preferred label moiety is nonaromatic, and the most preferred label moiety is biotin.

Examples of preferred labeling reagents for preparing the probes of this invention include:

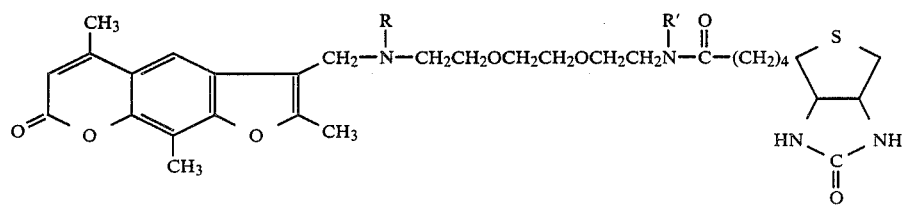

where R and R' are independently —H;

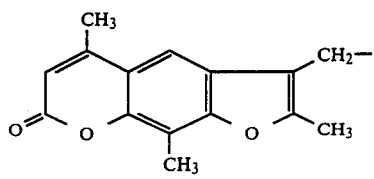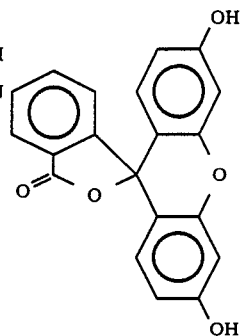

where R and R' are as defined above;

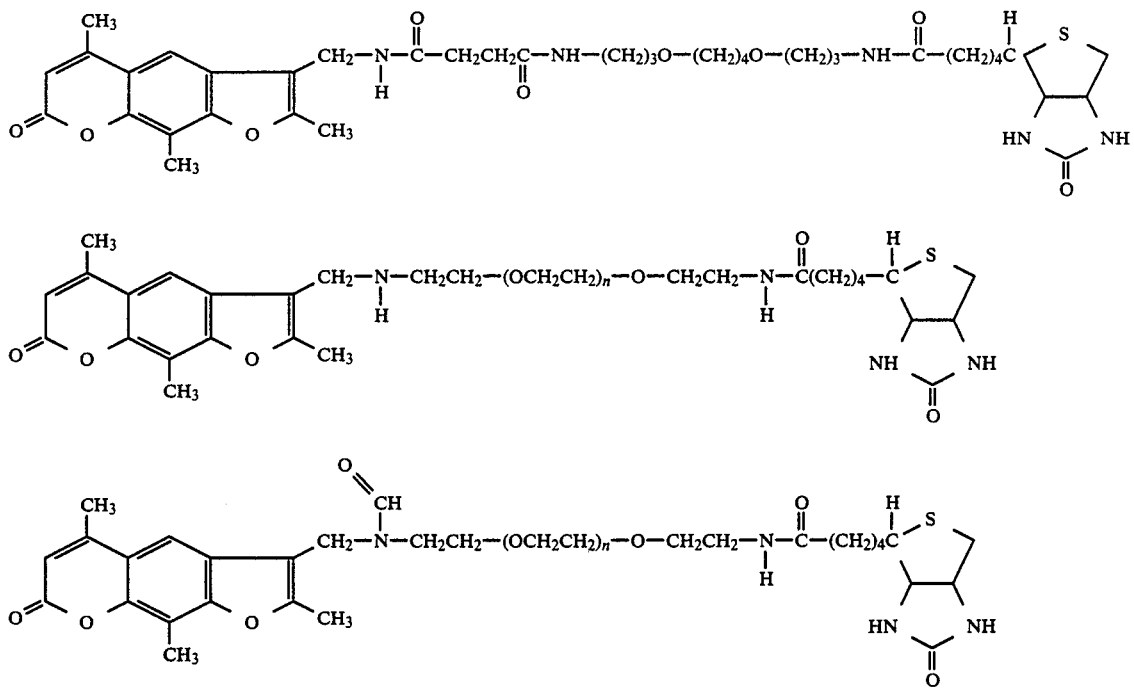

and

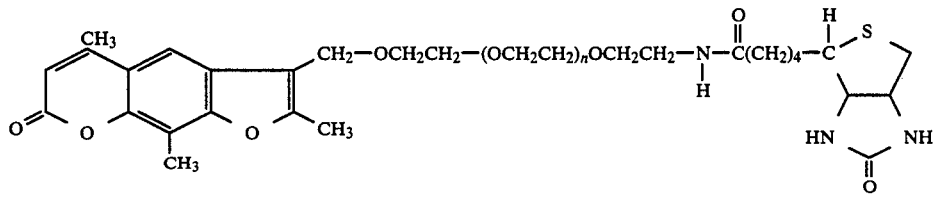

wherein n is an integer of from 1-4, and most preferably 2. The compounds where n is 2 are the most preferred, because they are easy to prepare, lack steric hindrance to interaction with the stacked base pairs of double-stranded nucleic acids, and exhibit improved incorporation into DNA. The third-to-last-named and the last-named derivatives where n is 2 are particularly preferred.

In one method, the reagents herein may be prepared in two steps wherein the alkylating intercalation moiety is attached to the spacer arm, and the resultant compound is reacted to attach the label moiety thereto. For example, the precursor:

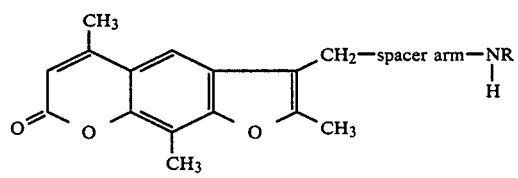

(where the alkylating intercalation moiety is 4'-methylene-4,5',8-trimethylpsoralen) may be prepared by methods which depend on what the spacer arm is.

If the spacer arm contains terminal amino groups

it may be attached to the 4'-methylene group of the 4,5',8-trimethylpsoralen derivative by the two-step method described by Saffran et al., *Proc. Natl. Acad. Sci. USA*, 79, 4594 (1982). In that method, a hydrocarbon or polyether hydrocarbon chain terminated on each end with halide groups, preferably chloride groups, which is either commercially available or readily prepared, is reacted with methylamine to form the corresponding chain with methylamino groups on both ends instead of halide groups. This compound is then reacted with chloromethyltrioxsalen, which is commercially avaiIabe, to form the desired precursor.

For example, the precursor:

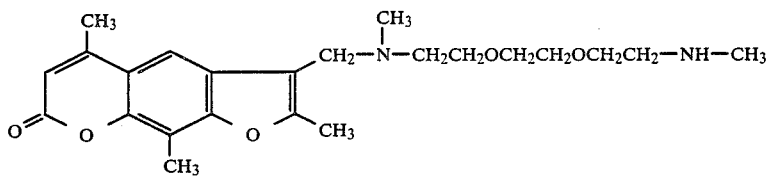

is prepared by reacting Cl—(CH$_2$CH$_2$O)$_2$—CH$_2$CH$_2$Cl with methylamine at 85° C. for 3-5 days to form CH$_3$NH(CH$_2$CH$_2$O)$_2$—CH$_2$CH$_2$—NHCH$_3$, which is in turn reacted with chloromethyltrioxsalen at 110° C. for 15 hours to form the precursor.

In the second step of this first method for preparing the labeling reagents the precursor as described above is reacted with the appropriate label moiety. This is accomplished by reacting a labeled compound which has a terminal group reactive with the terminal group of the spacer arm, and thus the reaction conditions will depend on the particular spacer arm and label moiety employed. For example, if the precursor has a terminal amino moiety it will react with an active ester of d-biotin, such as d-biotin p-nitrophenyl ester, when contacted therewith at temperatures of from about 20° to 40° C., preferably room temperature, for about 60 to 120 minutes, preferably 60 to 90 minutes, to release alcohol as a by-product. A suitable solvent such as dichloromethane is typically employed. Reaction progress may be monitored using thin-layer chromatography where the plate is sprayed with ninhydrin to detect disappearance of the starting material.

As another example, a precursor with the terminal amino moiety (e.g., —NHCH$_3$) will react with fluorescein isothiocyanate in mixed 1:1 THF:pyridine or solvents of similar polarity to insert thereon a label moiety detectable by fluorescence, at temperatures of from about 20° to 40° C., preferably room temperature, for about 8 to 12 hours, or until the product is detected. The compound selected to introduce the label moiety into the precursor is preferably such that it makes the final reagent capable of covalently crosslinking the nucleic acid when inserted therein. This is the case when active esters of d-biotin or fluorescein isothiocyanate are employed.

If the spacer arm contains internal groups which may be reactive with the alkylating intercalation moiety, these groups may be masked during preparation of the precursor before the label moiety is introduced. Thus, for example, one compound herein containing a spacer arm with an amide group and biotin as the label moiety may be prepared by a series of steps where 4,9-dioxa-1,12-dodecanediamine is reacted with di-t-butyl dicarbonate in methanol to produce the compound:

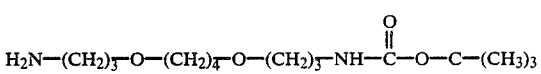

which is masked with a tert-butyloxy carbonyl group. This compound is in turn reacted with succinic anhydride to form the compound:

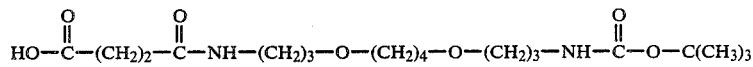

This compound is reacted with aminomethyl trioxsalen hydrochloride to yield:

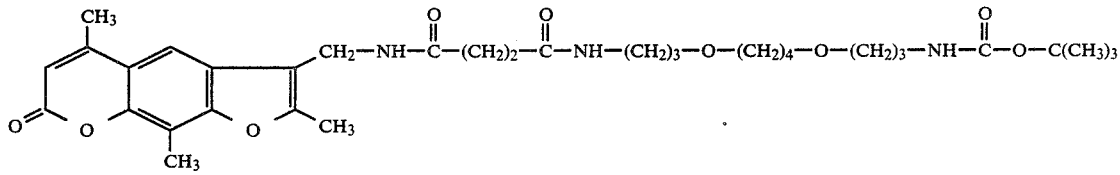

which, in the presence of an excess amount of formic acid, becomes the precursor by losing the masking carbamate (or t-BOC) group, and thereby terminating with a primary amine. This precursor may then be reacted with an active ester of d-biotin such as d-biotin p-nitrophenyl ester under conditions as described above or with another label moiety which is reactive with a terminal —NH$_2$ group to form the final compound.

The compound, 1-(biotinylamino)-13-(4,5',8-trimethylpsoralen-4'-yl)-3,6,9,12-tetraoxa-tridecane, is prepared by a similar method wherein tetraethylene glycol, or the appropriate polyethylene glycol for higher homolog chains, is reacted with paratoluene sulfonyl chloride in pyridine to yield the mono-tosylate alcohol, which when heated with lithium azide affords the corresponding azido alcohol, which in turn is reduced to the corresponding amino alcohol. The amino alcohol is then converted to the mono-tert-butyloxy carbonyl protected derivative using di-tert-butyl dicarbonate in tetrahydrofuran. The protected derivative is then reacted with chloromethyl trioxsalen to yield the psoralen derivative:

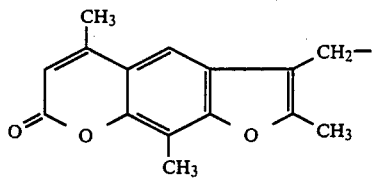
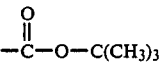

where n is 2 if tetraethylene glycol was employed initially. This compound, in the presence of trifluoroacetic acid in acetonitrile in the dark, becomes the primary amine terminated precursor as described above, which can then be reacted with, e.g., the N-hydroxysuccinimide ester of biotin or another appropriate label.

In a second method the labeling reagents herein may be prepared by reacting the spacer arm with the label moiety to form a precursor which is then reacted with a reagent supplying the alkylating intercalation moiety (e.g., a substituted trioxsalen reagent such as chloromethyl- or aminomethyltrioxsalen) to form the final compound. For example, the biotin-containing compound containing an amide group in the spacer arm may not only be prepared by the method described above, but also may be prepared by reacting the intermediate:

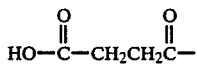

prepared as described above, with d-biotin in a solvent at about 70°–90° C. until the reaction is complete, then allowing the product to stand at room temperature with an excess amount of formic acid to remove the carbamate (t-BOC) group. The product, terminating with a primary amine group, is then reacted with succinic anhydride to introduce the amide functionality and a carboxylic acid group at the end. The resulting precursor, with the formula:

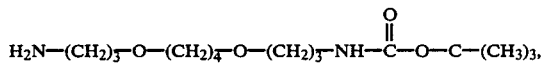
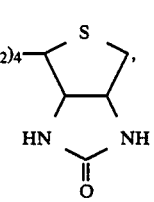

is finally reacted with aminomethyltrioxsalen hydrochloride at room temperature in the presence of a water-soluble carbodiimide to form the final product. Alternatively, the carboxyl group may be converted to an active ester (such as N-hydroxysuccinimide) and be subsequently reacted with aminomethyltrioxsalen hydrochloride. This latter method of synthesis is preferred, at least when psoralen reagents are employed, because less of the costly aminomethyltrioxsalen compound is expended.

The practitioner will recognize that other labeling compounds as defined herein can be prepared by similar techniques, depending on the particular reagents employed, by adapting the chemistry appropriately.

One useful specific application of the labeling reagents described above which are detectable by fluorescent or chromogenic detection means is in labeling specific regions or bands of chromosomes by staining the regions with the reagent and detecting the reagent, using the known chromosome banding technique described in the art for the Giemsa reagent. By thus distinguishing between or among chromosomes one can study chromosome anomalies such as Down's syndrome.

Another useful application of the reagents described above is in labeling nucleic acids. Generally this technique involves two steps: (1) contacting the nucleic acid with one or more of the reagents in such a way to cause the alkylating intercalation moiety thereof to intercalate into the nucleic acid to form a complex between the two, and (2) activating the complex in such a manner that the alkylating intercalation moiety of the reagent bonds covalently to one or both of the nucleic acid strands. Basically, the first step (intercalation) is preferably carried out by incubating the nucleic acid with the reagent(s) at about 0° to 50° C., preferably about 4 to 20° C., in a medium containing a buffer and having a pH of between about 6 and 9, preferably between about 6 and 8. The incubation generally will not require more than about 10 minutes. The buffer may consist of any buffer useful for this purpose such as, e.g., 10 mM Tris-HCl at pH 7.0 and 0.1 mM EDTA.

After the nucleic acid has been incubated for a sufficient period of time to intercalate the alkylating intercalation agent, the nucleic acid containing complex is, in the same medium, activated by such means as, e.g., reduction, irradiation, protonation or the like, depending on the alkylating intercalation moiety, for a sufficient period of time and under suitable conditions to ensure covalent bonding. The skilled practitioner will recognize what particular conditions are necessary given a particular moiety whose alkylating properties are described in the art. If the moiety is a psoralen derivative, for example, the complex is irradiated with UV light, preferably at about 350 to 390 nm wavelength, and more preferably at about 360 nm, at 1 to 100 mWatts per cm² for from 1 minute to 24 hours, to ensure covalent bonding.

The resultant nucleic acids will be labeled so that the label moiety can be detected by, for example, spectroscopic, photochemical, chemical, immunochemical or biochemical means. Thus, the labeled nucleic acid(s) may be subjected to, e.g., ultraviolet light to stimulate fluorescence or contacted with a polypeptide, lectin or antibody depending on the label moiety in the labeling reagent. In addition, the detection means may consist of a combination of an absorber-emitter moiety and a chemiluminescent catalyst in sufficient close proximity to each other to permit non-radioactive energy transfer, in conjunction with chemiluminescent reagents suitable for inducing a light response in the presence of the chemiluminescent catalyst, as described in European Patent Publication No. 0,070,686 published Jan. 26, 1983 and in European Patent Publication No. 0,070,685 published Jan. 26, 1983. Preferably the detection means is non-radioactive to obviate the difficulties associated with radioactive probes.

The degree of incorporation of these labeling reagents into nucleic acids can be measured by introducing a tritium atom into the compound as described in the experimental section. Nucleic acid incorporation of tritiated reagents can be determined by liquid scintillation counting or by autoradiography, which detection techniques are known in the art.

The nucleic acid itself which may be labeled by this technique may be any nucleic acid which can be subjected to intercalation and activation of alkylation, such as DNA, RNA, hybrids of DNA and RNA, and the like. Preferably the nucleic acid is DNA. For the purpose of labeling, the nucleic acid may be single or double stranded, or contain regions of single strands and double strands. More than one type of single-stranded or double-stranded nucleic acid may be present in the incubation broth for intercalation, and the presence of proteins in the broth will not interfere with intercalation. Thus, for example, the preferred psoralen derivative herein is capable, depending on the label moiety, of crosslinking, for example, one DNA strand to another DNA strand or one RNA strand to another RNA strand, or one RNA strand to one DNA strand.

A particularly useful application for the labeling reagents herein is in preparing a labeled nucleic acid hybridization probe (preferably non-radioactively labeled) for detecting nucleic acid sequences (RNA and/or DNA) such as, e.g., those characteristic of a pathogenic microbe or those responsible for or linked to a genetic disease. Pathogens would include infectious disease causing microorganisms or microorganisms involved in food spoilage. With such a probe, the method of probe preparation will be the same as described below for the M13 probe, but the nucleic acid will comprise a double-stranded region adjacent adjacent a single-stranded hybridization region which will act to detect by hybridization the nucleic acid sequence desired. A DNA of the latter description may be prepared by the method described by Brown et al., *Gene,* 20, 139-144 (1982) where the DNA of the hybridizing region complementary to the sequence to be detected is inserted into the double-stranded form of a virus known as M13, which is publicly available. After transformation, a single-stranded form of M13 can be prepared containing the hybridizing region which is complementary to the sequence to be detected. The recombinant M13 is then rendered partially double-stranded by primed synthesis using a synthetic oligonucleotide primer complementary to a region 5' to the cloning site and DNA polymerase I. The M13 probes then obtained are separated from impurities, including free triphosphates, by chromatography. More specific details can be found in the Materials and Methods section of the Brown et al. article, supra, the entire disclosure of which is incorporated herein by reference. The probes thus obtained are then subjected to intercalation and irradiation with the labeling reagent as described above.

Other probes obtained by different methods may be employed as the nucleic acid to be treated, provided that they contain a single-stranded region capable of hybridization with the complementary nucleic acid sequence which is to be detected by the probe. One such method, called the "gapped circle" technique, is described by Courage-Tebbe et al., *Biochim. Biophys. Acta,* 697 (1982) 1-5 and Everett et al., *The EMBO Journal,* 1 (1982) 433-437, the entire disclosures of which are incorporated herein by reference. This method involves in vitro hybridization of plus- and minus-strands derived from different phage strains to produce circular double-stranded phage M13 DNA containing gaps of defined size and location. More specifically, it involves (a) inserting a DNA fragment which contains a sequence complementary to the sequence to be detected into the bacteriophage M13 genome at a restriction site therein and preparing therefrom circular single-stranded DNA containing the DNA fragment;

(b) cleaving double-stranded M13 DNA which does not contain a DNA fragment insert at a restriction site which is less than 100 base pairs from, or is the same as, the restriction site used to insert the DNA fragment in step (a);

(c) denaturing the cleaved double-stranded M13 DNA;

(d) hybridizing the circular single-stranded M13 phage isolated from step (a) with the denatured double-stranded M13 DNA; and (e) removing any single-stranded DNA from the mixture to obtain a circular partially double-stranded DNA.

More specifically, in this process the M13 phage enters the bacterial host cell via pilus and single-stranded DNA is converted to the transient M13 replicative form (RF) double-stranded DNA, which is used as a cloning vector. A fragment of DNA from any source, preferably a cloned foreign DNA fragment, is inserted into a suitable restriction enzyme site in the cloning region within the M13 RF DNA after the RF DNA is cleaved with the appropriate restriction enzyme. M13 RF DNA carrying such a double-stranded insert is introduced into a suitable competent host cell such as *E. coli* by a transformation step. Growth of the host produces the hybrid molecule in both double-stranded and single-stranded (mature virus) forms. The single-stranded form with the cloned insert is then separated by separate culturing and isolated. The cloning procedure of step (a) is described in more detail by Messing, J. (1981) *Third Cleveland Symposium on Macro-Molecules: Recombinant DNA,* Ed. A. Walton, Elsevier, Amsterdam, p. 143-153, and summarized in the Amersham Corporation publication entitled "M13 Cloning and Sequencing Handbook" (5/83) beginning at page 8.

Preferably, the restriction site in step (b) is less than 50 (more preferably less than 20) base pairs from, or is the same as, the restriction site used to insert DNA fragment in step (a).

Another such method involves cutting a plasmid in the insert region with a restriction endonuclease, and then treating the resulting linearized fragment with exonuclease III to render it partially single-stranded.

It is preferred herein that the alkylating intercalation moiety of the reagent bond covalently to both strands of any double-stranded nucleic acid region present, i.e., that the nucleic acid be irreversibly crosslinked. Crosslinking is preferred because it renders the hybridization probe more stable to stringent hybridization conditions such as high temperatures and/or low salt content in the media which are desirable in detecting the nucleic acid sequences. The trimethylpsoralen compounds are preferred herein because of their crosslinking efficiency.

The probes herein can be used to detect specific nucleotide sequences of bacterial, viral, fungal, yeast, mammal, or parasite origin in clinical samples, whether located in chromosomes, fixed cells, body fluids, viral samples, or tissue sections. When the presence of a specific nucleic acid molecule is ascertained by the probe, one can diagnose nucleic acid-containing etiological agents in a patient. Examples of organisms which might be detected by the probe herein include *Chlamydia trachomatis, Neisseria gonorhoeae,* toxicogenic *E. coli* organisms, etc. The probe herein also provides a method for screening bacteria to determine antibiotic resistance.

The process herein can also be used to detect genetic diseases such as HLA-linked diseases, thalassemias and sickle cell anemia. The deoxyribonucleic DNA sequence whose presence or absence (in the case of some thalassemias) is associated with the disorder can be detected following hybridization with the probe herein which is detectable using polypeptides, based on complex formation with the detectable polypeptide.

Hybridization can also be used to determine paternity.

In addition, the probes herein may be used for the gene mapping (cytogenetics) by in situ blotting hybridization methods.

In addition, the probe herein represents a useful research tool in analyzing target nucleic acids, especially DNA. The details of these various methods to which the probe may be applied are described further in European Patent Application No. 0,063,879 to Ward et al.

The method by which the nucleic acid sequences are detected may be any method utilizing hybridization in conjunction with label detection of the probe. For example, the detection may be via a homogeneous assay method as described, e.g., in European Patent Publication No. 0,070,687 published Jan. 26, 1983 or in European Patent Publication No. 0,070,685 published Jan. 26, 1983, the entire disclosures of which are incorporated herein by reference.

One heterogeneous hybridization assay method which may be employed herein is described in U.S. Pat. No. 4,358,535, the entire disclosure of which is incorporated herein by reference. In this method of single-stranded nucleic acid sequence to be detected is affixed to an inert support and hybridized by the probe. If the process involves HLA typing, genomic HLA DNA from an individual is digested with a restriction endonuclease which produces a polymorphic digestion pattern with HLA DNA and the digest is subjected to gel electrophoresis. The product of gel electrophoresis is then transferred to an inert support such as a membrane and the following general procedure is employed. In a general method a cell, body fluid, viral or tissue sample suspected of containing the nucleic acid(s) to be detected is placed on an inert support, which may be contacted with a nutrient source such as a nutrient-containing agar to expand the number of cells to form distinct colonies. The cells, body fluid, or viral or tissue sample, which may be grown before or after placement on the inert support, are then contacted with an amount of a reagent effective to open cells, body fluid, tissue, or viral capsids in the viral sample and separate the strands of the nucleic acid(s). This lysing and nucleic acid denaturing step may be conducted before, during, or after the cell, body fluid, viral or tissue sample is deposited on an inert support. Thus, for example, the sample may be treated with reagent after it is applied to the support, or it may be mixed with the reagent and then applied to the support, or the support may be impregnated with or placed on or in the reagent before the cell, body fluid, or viral or tissue sample is deposited thereon. The inert support on which the sample is deposited is preferably a water-insoluble porous support, and more preferably a filter such as, e.g., nitrocellulose or a nylon membrane. The preferred support is a microfilter which inhibits passage of the sample through the filter.

If the sample is first deposited on the support, as by spotting or spreading, the lysing step with reagent is preferably conducted such that the sample does not migrate and remains affixed at the site on the support where it was deposited. One way to accomplish the lysing is to place the inert support, isolate side up, onto a bibulous support saturated with the lysing reagent for a time sufficient to open the cells, body fluid, or viral or tissue sample and separate the strands. The preferred lysing agent herein is a base, more preferably dilute aqueous solutions of sodium hydroxide, because it also denatures the nucleic acid. Other reagents or factors which cause denaturing include organic reagents such as, e.g., alcohols, amides, ureas, phenols, sulfoxides, and the like, certain inorganic ions such as thiocyanate or perchlorate, and elevated temperatures. The concentration and amount of reagent employed for this purpose will depend on whether the nucleic acids are DNA, RNA or hybrids of DNA and RNA.

In the next basic step a substantially (e.g., at least 80%) single-stranded form of the nucleic acid or acids is affixed on the support. Before the fixation step, however, a neutralizing step is preferably carried out wherein generally the inert support is placed, isolate side up, onto a bibulous support saturated with an aqueous buffer, generally of about pH 6 to 8, depending mainly on the denaturing and lysing regent(s) employed. If, for example, a base was employed, the cell sample is placed in a neutralizing buffer of about pH 6–8 with 1.0M to 4.0M NaCl to remove the base. More than one such neutralizing treatment may be conducted.

In the fixation step, the single-stranded form of the nucleic acid(s) is affixed on the support by any means known in the art. One such method involves exposing the cell, body fluid, or viral or tissue sample to UV light or to a drying solvent or sufficient heat to dry the sample, preferably from about 50° to 90° C. Drying to remove liquid from the support may be accomplished, for example, by baking or by washing with ethanol.

Once the nucleic acid(s) is affixed, it can be assayed by contact with an effective amount of the hybridization probe herein under hybridization conditions. Preferably, the hybridization step is preceded by a prehybridization step wherein the affixed sample is contacted with an amount of a reagent effective to prevent nonspecific reaction of the support with the probe to be employed. In this prehybridization step the support is incubated at room temperature or at an elevated temperature with the prehybridization reagent solution and usually gently stirring for a time sufficient to wet the support thoroughly. The reagent solution employed for this purpose preferably comprises from about 10 to 80 volume percent, more preferably about 50 volume percent, of an inert polar organic solvent. An example of a preferred hybridization solution for this purpose is one consisting of about 50% formamide, about 0.5 to 1M sodium chloride, about 0.05 to 0.1M sodium citrate, about 0.15 to 1.0% sodium dodecyl sulfate, and about 0.0001 to 0.010M EDTA buffer at pH 6-9, about 0.001% to 1% wt/vol of Ficoll (about 300-500 kdal), about 0.001 to 1% wt/vol of polyvinylpyrrolidone (about 250-500 kdal), and about 0.001 to 1% wt/vol of serum albumin. Also generally present in the solution are about 0.01 to 0.5 mg/ml of sonicated denatured DNA and optionally from about 0.5 to 2% wt/vol glycine. Optional components which may be present include dextran sulfate of from about 100 to 1,000 kdal in an amount of about 1 to 10 weight percent of the solution for best results. Other reagent solutions for this purpose include, e.g., ovalbumin, polyvinylpyrrolidone, Ficoll, transfer-RNA, herring sperm DNA or other similar reagents in a citrate or phosphate buffer of pH 6-9.

After the prehybridization step the probe is added to a hybridization solution, which is essentially the same as the prehybridization solution described above, with minor variations and usually including dextran sulfate. The particular hybridization solution chosen will depend mainly on the specific hybridization conditions employed, such as temperature. The amount of probe in the solution will depend on the label, the amount of probe which can be bound to the filter, and the hybridization conditions. Generally, excess over stoichiometric amounts of the probe relative to the sample DNA is present to enhance the rate of binding of the probe to the affixed nucleic acid sequence.

Hybridization conditions may have varying degrees of stringency depending on the ultimate goal desired. Stringency is affected by temperature, probe length, ionic strength, etc. Changing the concentration of formamide in the solution from about 20% to 50% will alter the polarity and thus the stringency of the hybridization. Generally the hybridization will occur at about 25° to 75° C., preferably 35° to 65° C., for 0.25 to 50 hours, preferably 15-24 hours, these conditions being dependent mainly on the concentration of the specific probe and nucleic acid sample employed, as well as the concentration of other ingredients in the medium. One skilled in the art of hybridization will be able to make the appropriate adjustments in conditions. The greater the stringency of the conditions, the greater the required complementarity for hybridization between the probe and the single-stranded nucleic acid.

After the hybridization step the cell, body fluid, or viral or tissue sample for the heterogeneous assay procedure is washed of unhybridized probe by adding to it a washing solution. Typically, the washing solution consists of sodium chloride, sodium citrate and sodium dodecylsulfate in amounts analogous to those used for the hybridization solution. The contact time for washing varies mainly with the type of solution but generally ranges from about 5 minutes to 3 hours or more. The support on which the sample is deposited may then be rinsed at room temperature with dilute sodium citrate-sodium chloride solution before it is subjected to detection means.

The probe itself can be detected by treating it with a means by which the label moiety is capable of being detected and determining the presence of the probe using an appropriate detection technique. Detection means are those described above for the label moieties and include spectroscopic, photochemical, immunochemical, biochemical or chemical means. Immunochemical means include antibodies which are capable of forming a complex with the probe under suitable conditions, and biochemical means include polypeptides or lectins capable of forming a complex with the probe under the appropriate conditions. The antibody, polypeptide or lectin must be capable of detection or include a moiety which can be detected when the complex is formed. Examples of such includable detectable moieties include fluorescent dyes, electron dense reagents or an enzyme capable of depositing an insoluble reaction product or being detected chromogenically. Usually the antibody, polypeptide or lectin will be coupled to an enzyme which will react with a chromogenic substrate. Using an avidin-enzyme or streptavidin-enzyme complex, for example, to detect hybridized probe labeled with biotin involves washing off the unreacted avidin-enzyme or streptavidin-enzyme complex, adding a chromogenic substrate for the enzyme, and reading the resulting color change. If the enzyme is horseradish peroxidase, the substrate may be 3,3',5,5'-tetramethylbenzidine. Detection of this substrate and other benzidines as meriquinone salts or immobilized complexes is described more fully in copending U.S. patent application Ser. No. 784,329, filed Oct. 4, 1985 entitled "Ionic Compounds Containing The Cationic Meriquinone Of A Benzidine" to W. Bloch et al., the disclosure of which is incorporated herein by reference. Proteins which become luminescent when treated appropriately may also be employed in detection of the labeled probe.

For HLA typing, the restriction fragment pattern of the unknown sample can be compared with the restriction fragment pattern of a known sample. The molecular weights of the restriction fragment can be determined by comparison to a molecular weight marker mix.

For added sensitivity of detection, the probes herein may also be used in conjunction with a polymerase chain reaction for amplifying target nucleic acid sequences utilizing primers and nucleotides and DNA polymerase to synthesize primer extension products which are utilized as templates to produce additional target sequences. This technology is described more fully in copending U.S. application Ser. No. 716,975 filed Mar. 28, 1985 to K. Mullis, the disclosure of which is incorporated herein by reference.

The following examples illustrate specific embodiments of the invention, which are not intended to be limiting to any degree. In the examples the percentages and parts are given in weight units unless otherwise noted and the temperatures in degrees Celsius unless otherwise noted. Correct elemental analysis signifies a discrepancy between calculated and found values of no more than 0.4%.

EXAMPLE 1

Preparation of N,N'-Dimethyl-(N-Biotinyl,N'-4'-methylenetrioxsalen)-3-6-Dioxa-1,8-Octanediamine, a Biotinylated Psoralen Reagent [hereinafter called Compound II (BP1)]

To a partial solution consisting of 216 mg of d-biotin p-nitrophenyl ester in 1.25 ml dichloromethane was added 222 mg of the compound [hereinafter referred to as Compound I]:

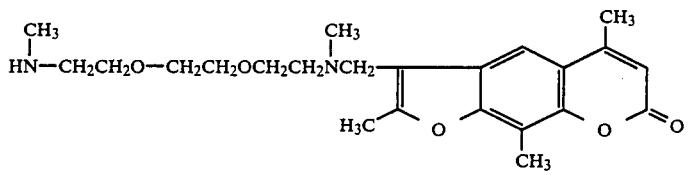

in a solution containing 650 μl of dichloromethane. This compound was prepared by the method described by Saffran et al., *Proc. Natl. Acad. Sci.*, 79, 4594–4598 (1982), the disclosure of which is incorporated herein by reference. In this method, a total of 20 grams of 1,2-bis(2-chloroethoxy)ethane and 165 g of methylamine (40% in water) were placed in a pressure bottle and heated to 85° C. for 3 days. The solution was made basic with NaOH and the product, 1,2-bis-(2-methylaminoethoxy)ethane, was extracted into chloroform and dried over anhydrous sodium sulfate. After evaporation of the solvent, the product (76% yield) was purified by vacuum distillation.

A mixture of 176 mg of chloromethyltrimethylpsoralen, which is commercially available, and 1.69 g of 1,2-bis(2-methylaminoethoxy)-ethane as prepared above was refluxed with stirring in 20 ml of dry toluene overnight. The reaction was monitored by thin-layer chromatography on silica gel with benzene/methanol, 1:1 (vol/vol), or 95% ethanol/concentrated aqueous ammonia, 4:1 (vol/vol), as eluants. The product (140 mg) was eluted from a silica gel (60–200 mesh) flash column with 95% ethanol/concentrated aqueous ammonia, 4:1, as a pale yellow oil, identified as Compound I by UV spectrum and comparison with a standard on TLC, and also by correct elemental analysis for C, H and N.

After the mixture of d-biotin p-nitrophenyl ester and Compound I was stirred for 45 minutes at room temperature, an additional 50 mg of the biotin ester was added. Reaction process was monitored by silica gel thin-layer chromatography using 1:1 benzene:methanol as solvent. Disappearance of the starting material was followed by spraying the plate with ninhydrin. The reaction mixture was applied to two 2 mm silica gel plates and the plates were developed with 8:1 chloroform:methanol. Each plate was developed to within 10 cm of the top, dried and redeveloped using the same solvent system. This step improved resolution of the product band. The product was fluorescent under long wave (>350 nm) ultraviolet light and was ninhydrin negative. The product band was scraped from the plates and eluted from the silica gel with methanol. The methanol was concentrated to yield 410 mg of a slightly yellow oil, which was then dissolved in 2.5 ml hot isopropanol, treated with 400 μl of 1N HCl, and allowed to cool. Crystals were formed and were removed by filtration. The hygroscopic product, Compound II, was submitted for elemental analysis:

Calc. for the dihydrate of the hydrochloride salt: C, 55.41%; H, 7.19%; N, 7.83%. Found: C, 55.89%; H, 7.34%, N, 7.05%.

Preparation of Tritiated Compound II

In this example Compound II of Example 1 was treated to contain a tritium atom so that incorporation of the compound into DNA could be readily detected by liquid scintillation counting or by autoradiography.

A 0.5 ml aliquot of an aqueous solution containing 3.05 μg of d-[3,9-$^3$H] biotin with a specific activity of 40 Ci/mmole was lyophilized in a 250 μl silanized conical vial. To the residue was added 250 μl of a 2 mM solution of d-biotin in 95% ethanol. This mixture was lyophilized, the residue was dissolved in 10 μl of dry dimethylformamide (DMF), and the resulting solution was lyophilized. The residue was dissolved in 5 μl of dry DMF and to this solution was added 200 μg of 1,1'-carbonyldiimidazole. This mixture was then heated for about 15 minutes at 80° C. and allowed to cool. To the vial was added 1.1 mg of Compound I followed by 20 μl of a 250 mM solution of triethylamine in dry DMF. The vial was allowed to sit in the dark for three days. The DMF was removed under vacuum and the residue was dissolved in 10 μl of water and applied to a 2.5×7.5 cm RP-2 reversed-phase silica plate and developed with 65:35 acetone:water. The product band was scraped from the plate and the product was eluted three times with 500 μl methanol. The methanolic extract contained the product as well as an impurity believed to be the bis-urea formed from the reaction of two equivalents of the trioxsalen with one equivalent of the carbonyldiimidazole. The methanol was removed under vacuum and the residue was taken up in 20 μl of 95% ethanol and applied to two analytical (2.5×7.5 cm) silica gel plates. These plates were developed by running the solvent, 1:5 of acetonitrile:0.1N ammonium chloride, five times up the plate and drying the plate between each development. The product band was scraped and eluted from the silica gel three times with 500 μl of 40% aqueous ethanol. The combined extracts were dried and then reconstituted in 100 μl of 95% ethanol. The product was determined by thin-layer chromatography to be homogeneous and was produced in a yield (based on optical density at 250 nm) of 67.2 nmole or 13.1%. The specific activity of the tritiated product was 0.49 Ci/mmole.

EXAMPLE 2

Preparation of N,N'-Dimethyl-(N-4'-methylenetrioxsalen,N'-thiocarbonyl aminofluorescein)-3,6-Dioxa-1,8-Octanediamine, a Fluoresceinated Psoralen Reagent [hereinafter called Compound III]

To a mixture of 5 ml of tetrahydrofuran (THF) and 5 ml of dry pyridine was added 200 μl of triethylamine, 160 mg fluorescein isothiocyanate and 180 mg of Compound I. The mixture was stirred at room temperature overnight. The solvent was evaporated, the residue was taken up in a few milliliters of chloroform, and the solution was applied to two 2 mm silica gel plates (20×20 cm). The plates were developed twice for two hours each time using as solvent 4:1:1:1 chloroform:n-butanol:acetone:formic acid. The product band was scraped off and eluted three times with 50 ml methanol. The combined methanol extracts were concentrated to an orange oil which was dried by azeotropic distillation of toluene. The residue was crystallized from aqueous ethanol. Total yield of Compound III was 115 mg (37%), and the correct elemental analysis for C, H, N (as the monohydrate) was obtained.

EXAMPLE 3

(Comparative)

Preparation of 4'-[(Aminomethylcarbonyl)aminomethyl]-Trioxsalen, A Glycyl Aminomethyl Psoralen Reagent for Comparative Purposes [hereinafter called Compound VII]

To a suspension of 146.9 mg of aminomethyltrioxsalen, hereinafter designated Compound IV, which is commercially available, and 175 µl of triethylamine in 1 ml of dry THF was added 148.2 mg of N-tert-butyloxycarbonylglycine p-nitrophenyl ester of the formula, hereafter designated Compound V:

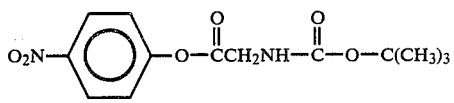

with stirring at room temperature. The suspension was stirred overnight and reaction progress was monitored by silica gel thin-layer chromatography using 5:1 dichloromethane:acetone. The reaction mixture was diluted with 5 ml of dichloromethane and extracted three times with 5 ml of 0.5N citric acid, three times with 5 ml of 5% sodium bicarbonate and three times with 5 ml of brine. The organic phase was dried over anhydrous potassium carbonate, filtered, and concentrated to a white residue, hereafter designated Compound VI, which was determined to be homogeneous by thin-layer chromatography. The residue weighed 100 mg, corresponding to a 48% yield. Correct elemental analyses were obtained for C, H, N.

Treatment of this compound VI with 98% formic acid gave a single product presumed to be the formate salt of the product, Compound VII.

Preparation of Tritiated Compound VII

A 250 µl aliquot of an ethanolic solution of commercially available tritiated aminomethyl trioxsalen, Compound IV (175 µg in 1 ml ethanol with 1.8 Ci/mmole activity) was dried and 10 µl of a 24 mM solution of triethylamine in dry DMF was added thereto. To this mixture was added 2 µl of a 250 mM solution of triethylamine in dry DMF. When no ninhydrin-positive material remained, the solvent was removed under vacuum and the residue was dissolved in 10 µl of a 10:1 chloroform:methanol mixture and applied to a 2.5×7.5 cm silica gel plate which was developed with 4:1 chloroform:methanol. Two bands were apparent under long-wave ultra-violet light, presumably the mono- and bis-adducts. The slower band corresponding to the desired product was scraped and eluted with 1 ml of methanol. The silica gel was removed by centrifugation and the supernatant was concentrated to a residue which was reconstituted in 20 µl of 98% formic acid and left to stand overnight. The formic acid was removed under vacuum and the yield of product was determined spectrophotometrically to be 29 nmole, 24%.

EXAMPLE 4

One Preparation of [N-Biotinyl,N'-(4'-Succinylaminomethyltrioxsalen)]-4,9-Dioxa-1,12-Dodecanediamine, a Biotinylated Psoralen Reagent With a 18-Atom Spacer Arm [hereafter called Compound XII (BP2)]

A. Synthesis of N-t-butyloxycarbonyl)-4,9-dioxa-1,12-dodecanediamine (Compound VIII)

To a solution of 10.22 g of 4,9-dioxa-1,12-dodecanediamine in 100 ml of methanol was added, with stirring at room temperature, a solution of 12 g of di-t-butyl dicarbonate in 25 ml of methanol. The addition was made dropwise. The mixture was stirred overnight and then dried to a residue under reduced pressure. The residue was dissolved in 100 ml of dichloromethane, and 35 g of silica gel was added to the solution. The dichloromethane was evaporated and the residue, adsorbed onto the silica gel, was fractionated on a column of silica gel using as eluent 70:30:5 chloroform:methanol:acetic acid. Fractions containing the product were pooled and concentrated and the residue was dissolved in 100 ml of water. The aqueous solution was extracted three times with 50 ml ether and then made basic to pH 11–12 with 6N sodium hydroxide and extracted four times with 75 ml of dichloromethane. The organic extract was dried over anhydrous potassium carbonate, filtered, and concentrated to a syrup weighing 5 g (yield of 33%). Correct elemental analyses of Compound VIII were obtained for C, H, N.

B. Synthesis of (N-biotinyl,N'-t-butyloxycarbonyl)-4,9-dioxa-1,12-dodecanediamine (Compound IX)

A total of 2.055 g d-biotin was suspended in 34 ml of dry DMF and the suspension was heated to 80° C., at which point the biotin had all dissolved. To this solution was added 1.38 g of 1,1'-bis-carbonyldiimidazole, and stirring and heating were contained for about 15 minutes until gas evolution ceased. The flask was allowed to cool for one hour and stirring was continued as a precipitate formed. To the resulting suspension was added 2.75 g of Compound VIII and stirring was continued for 16 hours. All material went into solution. The solvent was removed under vacuum and the residue was dissolved in 100 ml n-butanol and washed two times with 50 ml of 0.5N citric acid, 50 ml of saturated sodium chloride, 50 ml of 5% sodium bicarbonate and 50 ml of water. The alcohol was removed under vacuum and the residue was dissolved in about 50 ml of hot ethyl acetate. The solution was poured into 800 ml of hexane and the precipitate was removed by filtration and dried to yield a white powder weighing 3.755 g (84% yield). Correct elemental analyses of Compound IX were obtained for C, H, N as the monohydrate of the product.

C. Synthesis of (N-biotinyl)-4,9-dioxa-1,12-dodecanediamine (Compound X)

A solution of 1.06 g of Compound IX in 10 ml of 98% formic acid which was allowed to sit at room temperature until thin-layer chromatography using silica gel (4:1 chloroform:methanol) showed no remaining starting material. After 3.5 hours, the mixture was dried with a rotary evaporator. The residue was dissolved in 50 ml of water and the pH was adjusted to 12 using 6N sodium hydroxide. Ten grams of sodium chloride was added and the aqueous solution was extracted three times with n-butanol. The alcohol extract was dried over anhydrous potassium carbonate, filtered and evaporated to yield a residue (Compound X) which was used for subsequent reactions without further purification or characterization.

D. Synthesis of (N-biotinyl,N'-succinyl)-4,9-dioxa-1,12-dodecanediamine (Compound XI)

In 2 ml of pyridine was mixed 201 mg of succinic anhydride and 924 mg of Compound X as a HCl salt. The mixture was stirred overnight. The next day, thin-layer chromatography, using silica gel with 4:1 chloroform:methanol, showed no remaining starting material and the solvent was evaporated under reduced pressure. The residue was dissolved in 20 ml of DMF and 7 g of silica gel was added followed by about 500 ml of ether. The silica gel was removed by filtration and air dried. The gel was placed on top of a column of silica gel and the product was eluted with 4:1 chloroform:methanol containing a trace of acetic acid. Fractions containing the desired product were pooled and concentrated under vacuum. A white semicrystalline powder was obtained which was freed from residual acetic acid by azeotropic distillation of toluene. The yield of dry powder (Compound XI) was 363 mg (34%). Correct elemental analysis was obtained for C; calc: H, 8.08%; N, 10.21%; found: H, 7.51%; N, 9.66% (calculated for the monohydrate).

E. Synthesis of Compound XII

To a suspension of 210 mg of Compound XI in 3 ml of dry DMF was added 110 mg of aminomethyl trioxsalen hydrochloride followed by 60 μl of triethylamine. To this mixture was then added 72 mg of ethyl dimethylaminopropyl carbodiimide hydrochloride (EDAC). The suspension was stirred at room temperature in the dark and reaction progress was monitored by thin-layer chromatography using silica gel (4:1 chloroform:methanol). The mixture was partitioned between 50 ml n-butanol and 35 ml 0.5N citric acid. The butanol layer was separated and washed with 35 ml of 0.5N citric acid, with 35 ml of 5% sodium bicarbonate two times, and with 40 ml of brine. The alcohol solution was dried over magnesium sulfate, filtered, and concentrated to a foam. This dried material was dissolved in 2.5 ml of 95% ethanol and applied to a 2 mm silica gel plate which was developed with 10:1 chloroform:methanol. The product band was scraped and extracted with methanol, the methanol was concentrated, and the residue crystallized from isopropanol/water. Correct elemental analyses were obtained for Compound XII for C, H, N based upon values calculated for the dihydrate.

EXAMPLE 5

Preparation of Tritiated [N-Biotinyl,N'-(4'-Succinylaminomethyltrioxsalen)]-4,9-Dioxa-1,12-Dodecanediamine [Compound XII]

A. Synthesis of (N-t-butyloxycarbonyl,N'-succinyl)-4,9-dioxa-1,12-dodecanediamine (Compound XIII)

To a solution of 304.4 mg of Compound VIII (Example 4, A) in 1 ml of dry pyridine was added 100.1 mg succinic anhydride. All of the compound dissolved and reaction progress was monitored by thin-layer chromatography using silica gel (70:30:5 chloroform:methanol:acetic acid). Disappearance of starting material was followed by spraying the plates with ninhydrin. When no starting material remained, the reaction mixture was concentrated under vacuum, the residue was dissolved in 5 ml of dichloromethane, and the organic solution was washed three times with 5 ml of 0.5N citric acid. The organic layer was dried under vacuum to yield 540 mg of a syrup (Compound XIII) which was used for subsequent reactions without further purification or characterization.

B. Synthesis of [N-t-butyloxycarbonyl,N'-(4'-succinylaminomethyl trioxsalen)]-4,9-dioxa-1,12-dodecanediamine (Compound XIV)

To a solution of 323 mg of Compound XIII in 1 ml of dichloromethane was added 227 mg of dicyclohexyl carbodiimide. The mixture was stirred for 15 minutes and 321 mg of aminomethyl trioxsalen hydrochloride and 300 μl of triethylamine were added. The mixture was stirred in the dark at room temperature for 20 hours and then diluted with 50 ml of dichloromethane. The mixture was washed with 50 ml of 0.5N citric acid, 50 ml of 5% sodium bicarbonate and 50 ml of brine. The organic phase was dried over anhydrous potassium carbonate, filtered, and concentrated to a white residue. This material was homogeneous as determined by thin-layer chromatography using silica gel (4:1 chloroform:methanol) and the NMR spectrum was consistent with that anticipated for the desired product, Compound XIV.

C. Synthesis of N'-(4'-succinylaminomethyltrioxsalen)-4,9-dioxa-1,12-dodecanediamine (Compound XV)

The residue (Compound XIV) from the above reaction was dissolved in 10 ml of 98% formic acid and allowed to sit in the dark overnight. The excess formic acid was removed to yield a semicrystalline residue which was dissolved in 7 ml of hot ethanol and filtered. To the filtered solution was added ether until the cloud point was reached. The mixture was set in the cold. Crystals were removed by filtration to yield 250 mg. Correct elemental analysis could not be obtained from this material and it was used directly without further purification in the subsequent reaction.

D. Synthesis of Tritiated Compound XII

A 205 μl aliquot of a 2 mM ethanolic biotin solution containing 100 μg biotin was dried in a silanized 250 μl conical tube. In the same vial 500 μl of a solution of 3.05 μg tritiated biotin (40 Ci/mmole activity) was dried. The residue was dissolved in 10 μl of dry DMF and again dried. To the residue was added a 247 mM solution of 5 μl 1,1'-bis-carbonyl diimidazole in dry DMF. The vial was heated to 80° C. for 10 minutes, at which time 1.5 mg of Compound XV was added, followed by a 250 mM solution of 20 μl triethylamine in dry DMF. The solution was allowed to sit for two hours and was then dried. The residue was reconstituted in 20 μl of 25% methanol in chloroform and applied to two analytical (2.5×7.5 cm) silica gel plates. The plates were twice developed with 8:1 chloroform:methanol, with drying between each run. Product-containing bands were scraped and the product was eluted twice with 1 ml methanol. The product thus obtained was found to be homogeneous by thin-layer chromatography. The methanol was evaporated and the residue dissolved in 100 μl of 95% ethanol. The yield of product, tritiated Compound XII, was determined spectrophotometrically to be 283 nmole (67%). The specific activity of the product was 0.48 Ci/mmole.

EXAMPLE 6

Preparation of N-Biotinyl,N'-(4'-methylene trioxsalen)-3,6,9-trioxaundecane-1,11-diamine [Compound XVI (BP3)] and N-biotinyl,N'-formyl,N'-(4'-methylene trioxsalen)-3,6,9-trioxa-undecane-1,11-diamine [Compound XVII (BP4)]

A. Synthesis of Bis-O,O'-Tosyl-3,6,9-Trioxa-undecane-1,11-diol (Compound XVIII)

To a chilled solution of 42 g of tetraethylene glycol in 500 ml of dry pyridine was added 100 g of p-toluene sulfonyl chloride. The solution was stirred at 4° C. for 18 hours. To the solution was added 100 ml of methanol and stirring was continued for an additional hour. The mixture was poured into one liter of ice water. The water was decanted and the oily residue was partitioned between 300 ml of chloroform and 100 ml of water. The organic phase was washed with 0.5N citric acid (250 ml) and brine (250 ml). The organic extract was dried over magnesium sulfate, filtered and concentrated to a residue which was adsorbed onto 25 g of silica gel and fractionated on a column using chloroform:methanol 97:3 as eluant. Fractions containing the product were pooled and concentrated to a yellow syrup.

B. Synthesis of 1,11-Diazido-3,6,9-trioxa-undecane (Compound XIX)

To a solution of 50.3 g of Compound XVIII in 250 ml of dry dimethylformamide (DMF) was added 30 g of lithium azide. The mixture was heated to 80° C. with stirring until TLC on silica gel (chloroform:methanol 97:3) revealed no starting material remaining. The solvent was removed under vacuum and the residue partitioned between 500 ml of ether and 250 ml of brine. The ether layer was dried over magnesium sulfate, filtered and concentrated to an oil.

C. Synthesis of 1,11-Diamino-3,6,9-trioxa-undecane (Compound XX)

To a chilled, stirred solution of 24.4 g of Compound XIX in 250 ml pyridine was added 89 g of triphenyl phosphine. Nitrogen bubbles evolved. The solution was stirred with ice cooling for 45 minutes and then allowed to warm to room temperature. After 45 minutes at room temperature 100 ml of concentrated ammonium hydroxide was added and the mixture stirred overnight. The mixture was partitioned between 500 ml of 0.5N citric acid and 250 ml of ether. The aqueous phase was washed with ether ($2 \times 250$ ml) to remove triphenyl phosphine oxide. The aqueous phase was saturated with sodium chloride and extracted with 1-butanol ($4 \times 250$ ml) and dichloromethane ($4 \times 250$ ml). The combined alcohol and dichloromethane extracts were concentrated under reduced pressure and the residue was taken up in 100 ml of ethanol. Concentrated hydrochloric acid (15 ml) was added and the solvent removed under reduced pressure. The residue was crystallized from ethanol/ether. The hygroscopic crystals were dried under vacuum.

D. Synthesis of N-Tert-butyloxycarbonyl-3,6,9-trioxa-undecane (Compound XXI)

To a solution of 13.26 g of Compound XX and 8 ml of triethylamine in 100 ml of methanol was added a solution of 12 g of di-tert-butyl dicarbonate in 10 ml of methanol. Carbon dioxide bubbles evolved and the reaction mixture was slightly exothermic. Stirring was continued until gas evolution ceased. The solvent was removed under reduced pressure and the residue adsorbed onto 20 g of silica gel and fractionated on a column using dichloromethane:methanol:acetic acid 70:30:5 as eluant. The fractions containing product were pooled and concentrated to yield the mono-BOC (butyloxycarbonyl) derivative as a syrup.

E. Synthesis of N-(tert-Butyloxycarbonyl),N'-(4'-methylene trioxsalen)-3,6,9-trioxa-undecane (Compound XXII)

To a solution of 280 mg of Compound XXI and 120 mg of triethylamine in 4 ml of dry toluene was added 224 mg of chloromethyl trioxsalen. The mixture was heated at 110° C. overnight in the dark. TLC on silica gel using as eluant chloroform:methanol 8:1 showed no starting material remaining. The reaction mixture was adsorbed onto 5 g of silica gel and fractionated on a column using chloroform:methanol 8:1 as eluant. Fractions containing the product (fluorescent and ninhydrin positive) were pooled and concentrated to a syrup which spontaneously crystallized.

F. Synthesis of N-Biotinyl,N'-(4'-methylene trioxsalen)-3,6,9-trioxa-undecane-1,11-diamine (Compound XVI) and N-Biotinyl,N'-formyl,N'-(4'-methylene trioxsalen)-3,6,9-trioxa-undecane-1,11-diamine (Compound XVII)

A solution of 600 μmole of Compound XXII in 5 ml of 97% formic acid sat overnight at room temperature. This quantitatively removed the BOC protecting group. The solvent was removed under reduced pressure and the residual amine used without further purification. A solution of this amine in dry DMF (2.86 μmole in 25 μl) and 10 μl of a 1M solution of triethylamine in dry DMF was added to 1 mg of the N-hydroxysuccinimide ester of biotin. The solution sat in the dark for two hours at room temperature and was purified by preparative TLC on silica gel using as eluant chloroform:methanol 4:1. The low Rf product band which was fluorescent and contained biotin was scraped and washed with 1 ml methanol to elute the product, Compound XVI. The higher Rf band which also was fluorescent and was biotinylated was scraped off and eluted with 1 ml methanol. This material, Compound XVII, contained one biotin per psoralen and from mass spectral data is believed to be the mono-formyl derivative of Compound XVI. (These reactions were also utilized to synthesize tritium-labeled Compounds XVI and XVII using commercially available tritiated biotin N-hydroxysuccinimide ester as reagent.)

EXAMPLE 7

Preparation of 1-(Biotinylamino)-13-(4,5',8-trimethylpsoralen-4'-yl)-3,6,9,12-tetraoxa-tridecane [Compound XXIII (BP6)]

A. Synthesis of Mono-toluenesulfonyl Tetraethylene Glycol (Compound XXIV)

To a solution of tetraethylene glycol (42 g; 216 mmole) in 500 ml of dry pyridine cooled to 4° C. was added p-toluene sulfonyl chloride (50 g; 262 mmole). The solution was stirred in the cold overnight. The pyridine was evaporated and ca. 300 ml of tolune was used to azeotrope the pyridine. The residue was taken up in 60 ml of methanol and 30 g of silica gel was added. The solvent was removed under reduced pressure and the residue fractionated on a silica gel column using 97:3 chloroform:methanol as eluant. The mono-tosylate obtained was used directly for the next reaction.

B. Synthesis of 11-Azido-3,6,9-trioxa-undecanol (Compound XXV)

Compound XXIV was dissolved in 250 ml of dry dimethylformamide, and lithium azide (15 g; 306 mmole) was added. The mixture was stirred and heated to 80°–100° C. After several hours, thin layer chromatography (TLC) using 97:3 chloroform:methanol on silica gel showed all ultraviolet-absorbing material at the origin (lithium tosylate). The solvent was removed under reduced pressure and the residue was taken up in tetrahydrofuran, and 40 g of silica gel was added. The solvent was removed and the residue fractionated on a silica gel column using ethyl acetate as eluant. Fractions containing the product were pooled and concentrated. Correct elemental analyses were obtained for carbon, hydrogen and nitrogen. On TLC, the Rf of the product band on silica gel using ethyl acetate was 0.21.

C. Synthesis of 11-Amino-3,6,9-trioxa-undecanol (Compound XXVI)

To a solution of Compound XXV (15.94 g; 72.7 mmole) in 100 ml of pyridine was added triphenylphosphine (29 g; 111 mmole). After stirring for one hour, at which time gas evolution had subsided, 50 ml of concentrated aqueous ammonium hydroxide was added and the mixture stirred overnight. The reaction mixture was concentrated under vacuum and the residue partitioned between 200 ml of water and 200 ml of ether (aqueous layer at pH 2). The aqueous layer was washed twice with 200 ml ether each time. The aqueous layer was adjusted to pH 11 with solid sodium hydroxide and extracted three times with 150 ml n-butanol each time. The butanol extract was dried over sodium sulfate, filtered and concentrated. The residue was taken up in tetrahydrofuran and filtered. The filtrate was evaporated to a syrup which was azeotroped with toluene.

D. Synthesis of 11-tert-Butyloxycarbonylamino-3,6,9-trioxa-undecanol (Compound XXVII)

To a suspension of Compound XXVI (12 g; 62.1 mmole) in 100 ml of dry tetrahydrofuran was added di-tert-butyl dicarbonate (15 g; 68.7 mmole). Much gas was generated. Triethylamine (10 ml; 7.26 g; 71.3 mmole) was added and the mixture stirred at room temperature. When gas evolution ceased, the solution was diluted with methanol and 20 g of silica gel was added. The solvents were removed under reduced pressure and the residue was fractionated on a column of silica gel using 8:1 chloroform:methanol as eluant. Fractions containing the product were pooled and concentrated to a syrup. Correct elemental analyses were obtained for carbon, hydrogen and nitrogen.

E. Synthesis of 1-(tert-Butyloxycarbonylamino)-13-(4,5',8-trimethylpsoralen-4'-yl)-3,6,9,12-tetraoxa-tridecane (Compound XXVIII)

Chloromethyltrioxsalen (277 mg; 1 mmole) and lithium iodide (135 mg; 1.01 mmole) were mixed in 10 ml of dry tetrahydrofuran. The mixture was sonicated briefly. To the mixture was added Compound XXVII (293 mg; 1 mmole). A clear, yellow solution resulted. To the solution was added potassium tert-butoxide (115 mg; 1.03 mmole). A precipitate formed and the mixture was stirred in the dark and refluxed gently for several hours. The reaction was diluted with 2 ml of tetrahydrofuran, the suspension was centrifuged, and the supernatant was filtered through a 0.45 micron syringe filter. The filtrate was neutralized by the addition of three drops of glacial acetic acid. The solvent was removed under reduced pressure and the residue reconstituted in 2 ml of methanol. The solution was applied to four 20 cm×20 cm preparative silica gel plates. The plates were developed in ethyl acetate and the product bands were scraped from the plates and eluted into ca. 50 ml of methanol. The methanol extract was filtered and concentrated to dryness, reconstituted in 10 ml of methanol, and filtered by syringe through a 0.45 micron filter. A 7.96M solution was obtained which was used for further reactions. Correct elemental analysis for carbon, hydrogen and nitrogen was obtained. The Rf is 0.27 (silica gel; ethyl acetate).

F. Synthesis of 1-(Biotinylamino)-13-(4,5',8-trimethylpsoralen-4'-yl)-3,6,9,12-tetraoxa-tridecane (Compound XXIII)

Compound XXVIII (15.4 mg; 28.9 μmoles) was taken up in 1 ml of 2M trifluoroacetic acid in acetonitrile and allowed to sit at room temperature in the dark until thin layer chromatography using ethyl acetate on silica gel showed no starting material remaining. The solution was evaporated under reduced pressure and the residue dissolved in 100 μl of dry pyridine. To this solution was added biotion N-hydroxysuccinimide ester (NHS-biotin) (10 mg; 29.4 μmole). The mixture sat at room temperature in the dark for three days and was then taken to dryness and the residue dissolved in 500 μl of methanol. The mixture was centrifuged to remove a small amount of insoluble material. The supernatant was applied to a 20 cm×20 cm preparative layer silica gel plate, and the plate was developed with 90:10:5 dichloromethane:methanol:acetic acid. The product band was removed from the plate and eluted with methanol. The extract was filtered and taken to dryness. The residual material was submitted for high resolution mass spectral analysis. Found: Molecular weight=682.2781 ($C_{33}H_{45}N_3O_9S$+Na).

The Rf product band eluted at 0.33 (silica gel; 90:10:5 dichloromethane:methanol:acetic acid).

EXAMPLE 8

This example illustrates the effect of the length of the spacer arm and of amide and formal functional groups on the spacer arm, and of crosslinking on the extent of incorporation of the psoralen reagent into the DNA. It also illustrates hybridization of the probes.

A. Biotinylation of DNA Using Compound II (BP1) and XII (BP2) and Hybridization to Chlamydia Using Biotinylated Probes To determine the ability of the psoralen reagents to incorporate into DNA, a second strand was synthesized on single-stranded M13 phage DNA as described below, a procedure described by Brown et al., *Gene,* 20, 139-144 (1982), supra.

M13 clones were prepared using M13mp9, an M13 derivative which is publicly available from Bethesda Research Laboratories (BRL), P.O. Box 6009, Bethesda, MD 20977 USA. The M13mp9 is described on pages 88-89 of the 1983 BRL catalogue, and its cloning region is provided in FIG. 3A. The M13 clones were grown on publicly available *E. coli* strain JM101 as described in J. Messing et al., *Nucl. Acids Res.,* 9, 309-321 (1980). Templates used for primed synthesis in preparing the M13 probes were grown as described by Sanger et al., *J. Mol. Biol.,* 143, 161-178 (1980), with the following modifications: Early-log, 10-ml cultures of phage JM 101 were infected with 0.1 ml phage M13 stock ($10^{12}$ pfu/ml) and grown with vigorous shaking for no more than six hours. The infected cells were pelleted by centrifugation for 10 minutes at 10,000 rev./min. in a centrifuge and M13 was precipitated from the supernatant by adding 1/5 vol. of 10% polyethylene glycol 6000 in 2.5M NaCl. The phage was recovered by centrifugation for 10 minutes at 10,000 rev./min., and the pellets were resuspended in 200 μl of 10 mM Tris.HCl of pH 7.4 and 0.1M EDTA, and transferred to eppendorf microfuge tubes. The phage were disrupted by extraction with 100 μl phenol, and DNA was recovered from the aqueous phase by ethanol precipitation after the residual phenol was removed by ether extraction. The DNA was resuspended in 50 μl of 10 mM Tris.HCl and 0.1 mM EDTA and used as template to prepare M13mp9CHL2.1, which is a derivative of M13.

FIG. 1 shows a restriction map of the 7 kilobase *Chlamydia trachomatis* clone pCHL2 (publicly available plasmid) insert subcloned into the BamHI site of pBR 322. The map shows the origin of subclone M13mp9CHL2.1, which has an insert of 1500 base pairs. This 1.5 kilobase pair fragment, between the PstI and XmaI sites, was cut out with the enzymes PstI and XmaI and ligated into the PstI and XmaI sites in M13mp9 to yield the subclone M13mp9CHL2.1, shown as a restriction map in FIG. 2.

A 16-residue long oligonucleotide probe primer (d(CACAATTCCACACAAC)) was purchased from New England Biolabs.

An annealing mixture containing 2 μl of M13mp9CHL2.1 (3.7 μg/μl), 31.8 μl (2.5 μg/150 μl) of probe primer as described above, 16.3 μl of 10× Hin II buffer (100 mM Tris.HCl pH 7.4, 500 mM NaCl, 50 mM MgCl$_2$, 10 mM dithiothreitol (DTT)) and 3 μl water was added to a 0.5 ml plastic Eppendorf tube and heated for 2 minutes in a boiling water bath. Then it was allowed to anneal at 37° C. for 30 minutes.

To 14 μl of the annealing mixture was added 14 μl each of 0.3 mM dATP, dGIP, dCTP, and dTTP, 4 μl of 0.1M DTT, 1.8 μl water, 1 μl of 50 mg/ml of bovine serum albumin, and 2 μl of 2 U/μl of the Klenow fragment of E. coli DNA polymerase I. This mixture was incubated for 40 minutes at 30° C.

To determine if sufficient biotin labels for detection could be introduced into the DNA using the psoralen reagent, the amount of incorporation of psoralen was ascertained. Thin-layer chromatography (TLC) was used to quantify the amount of tritium-labeled biopsoralen introduced into the plasmid pBR 322, deposited with ATCC No. 37,017. For this measurement, 2 μg of pBR 322 were combined with 300 pmoles of Compound XII in 2 μl of 10 mM Tris-HCl pH 7.0 and 0.1 mM EDTA buffer and incubated at 4° C. for 60 minutes. Then the material was irradiated with 360 nm of ultraviolet light at an intensity of 34 mWatts per cm$^2$ for 1.0 hour. As a control for background, Compound XII in the absence of DNA was irradiated using the same conditions. Then, 0.5 μl of each of these two irradiated samples and 0.5 μl of non-irradiated Compound XII and DNA at 150 pmoles/μl and 1 μg/μl, respectively, were loaded onto a TLC plate and chromatographed using 50 mM NH$_4$Cl in 50% acetonitrile as a solvent. Autoradiography was used to determine the positions of the reaction components. The autoradiograph indicated that all of the non-irradiated Compound XII moved beyond the origin. In the lane loaded with Compound XII irradiated in the absence of DNA, almost all of the radioactivity moved beyond the origin, leaving only a small amount of material at the origin. As to the lane loaded with Compound XII irradiated in the presence of pBR 322 DNA, however, the autoradiograph showed a substantial amount of radioactivity at the origin of the lane, indicating that the psoralen might be sufficiently incorporated into the DNA to enable detection of the labels.

To determine the level of psoralen incorporation, the material was scraped from the TLC plates using the autoradiograph as a guide. After the scraped material was counted in scintillation fluid, the amount of biotinylated psoralen incorporated into DNA was estimated by taking the difference between the amount of radioactivity found at the origin of the sample which consisted of irradiated psoralen and DNA and the amount of radioactivity found at the origin of the sample which consisted only of irradiated psoralen. The number of biotinylated psoralen groups incorporated per base pair was determined by dividing the estimated amount of psoralen incorporated by the total amount of radioactivity recovered from the sample which contained both psoralen and DNA. Based on this method, about 10 biotin labels per 100 base pairs were incorporated. This amount of incorporation appeared to be adequate because steric hindrance would likely prevent an avidin or antibody detection system from binding to more than about 10 biotins per 100 base pairs.

The same procedure was used to test the level of incorporation for Compound II irradiated with pBR322 and for $^3$H labeled aminomethyltrioxsalen of the formula:

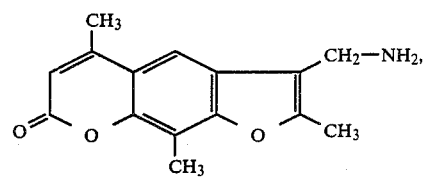

and unlabeled glycyl aminomethyltrioxsalen (with an amide group) (Compound VII):

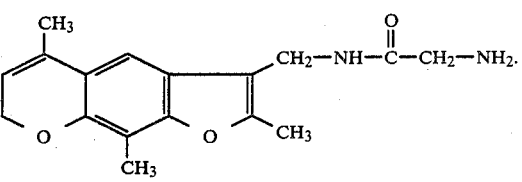

The results show that aminomethyltrioxsalen had the most incorporation, followed by Compound VII, Compound XII, and finally Compound II.

The avidin-binding ability of DNA hybridization probes labeled with biotin was then determined. For this purpose, two M13 DNA probes of this invention, those biotinylated with Compounds II and XII, were compared with a biotinylated deoxyuridine nucleotide with an 11-atom spacer arm (2'-deoxyuridine triphosphate 5-allylamine-biotin, or Biotin-11-dUTP obtainable from Enzo Biochem, Inc.) of the formula:

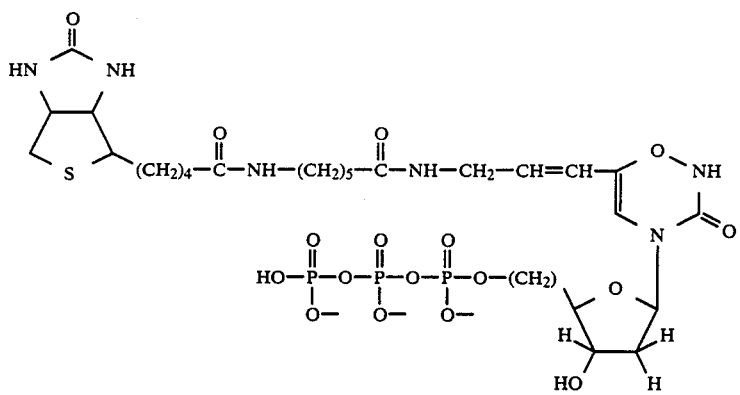

This compound is disclosed by European Patent Publication No. 0,063,879 to bind avidin efficiently after incorporation by nick-translation into DNA. To make this comparison it was necessary to use a method which allows both the incorporation of biotinylated nucleotides and psoralens and still leaves some DNA single-stranded so that it can be attached to a membrane or hybridized to a target DNA molecule. For this purpose, a mixture of 14 μl of the annealing reaction mixture described above, 14 μl each of 0.3 mM dATP, 0.3 mM dGTP, 0.3 mM dCTP and 0.3 mM bio dUTP as described above, 4 μl of 0.1M dithiothreitol, 1.8 μl water, 1.0 μl of 50 mg/ml bovine serum albumin, 2 μl of 2 U/μl Klenow fragment of polymerase I, and 5 μl of 1 mCi/ml (27.2 Ci/mmole) $^3$H labeled dCTP was incubated for 80 minutes at 30° C.

For labeling with psoralen, a similar reaction was performed by incubating 14 μl of the annnealing mixture, 14 μl each of 0.3 mM dATP, 0.3 mM dGIP, 0.3 mM dCTP, 0.3 mM dTTP, 4 μl of 0.1M dithiothreitol, 1.8 μl of water, 1.0 μl of 50 mg/ml bovine serum albumin, 2 μl of 2 U/μl Klenow fragment of polymerase I, and 5 μl of 1 mCi/ml dCTP for 40 minutes at 30° C.

The high molecular weight DNA products from both of these reactions were purified using a Sephadex G 50 column with a buffer of 10 mM Tris-HCl at pH 7.0 and 0.1 mM EDTA and collecting 0.5 ml fractions. In the case of the M13 plasmid labeled with bio dUTP and 3H dCTP, the DNA peak was found by counting fractions in a scintillation counter. The amount of DNA was quantified by the ethidium bromide spot assay described by T. Maniatis et al., *Molecular Cloning—A Laboratory Manual*, (Cold Spring Harbor Laboratory, 1982), pp. 468–469. The unlabeled M13 DNA which was to be labeled with Compounds II and XII was located in the column fractions and quantified by the ethidium bromide spot assay. The yield of both kinds of M13 DNA was about 700 nanograms.

For the purpose of labeling with Compounds II and XII, the fraction containing the 700 nanograms of unlabeled M13 DNA was split into two equal portions and dried. To one portion of M13 DNA, 427 pmoles of Compound II was added in a 70 pmole/μl of ethanol solution. To the other portion, 427 pmoles of Compound XII was added in a 28.3 pmoles/μl ethanol solution. These samples were again dried and then each was resuspended with 4 μl H$_2$O. The samples were then irradiated with 360 nm ultraviolet light at 12 mW/cm$^2$ for 80 minutes at 5° C. After irradiation, these samples were brought to a volume of 0.3 ml, with 100 mM NaCl, 10 mM Tris-HCl pH 7.0 and 0.1 mM EDTA. To remove the unincorporated Compounds II and XII, the samples were extracted several times with CHCl$_3$. Purity and yield were ascertained using the TLC system described above.

The M13 DNA was then labeled with tritiated Compounds II and XII by the incubation and irradiation procedure described above. The moles of biotin incorporated into the DNA were then measured by determining the amount of tritium counts present. In the case of the biotinylated dUTP as taught by European Patent Publication No. 0,063,879, this measurement assumes that the number of biotinylated uracil groups is proportionate to the number of tritiated dCTP nucleotides incorporated. From knowing the amount of tritiated cytosines incorporated and the ratio of tritiated to non-tritiated cytosines from the specific activity, one can determine the number of biotinylated uracil groups as being approximately the same as the number of cytosines incorporated. The amount of biotinylated uracil groups incorporated was found to be about 10 per 100 base pairs, whereas the amount of psoralen incorporated using tritiated Compounds II and XII for the reagent was about 5 per 100 base pairs.

In the next step for comparing availability to avidin, the biotin-labeled DNA probes were added to 1M Tris-HCl at pH 7 and 1.5M NaCl, and applied and fixed to a filter by spotting about 1 picomole of each, in terms of biotins, onto the filters and then dried at 80° C. for two hours. As a control, herring sperm DNA obtained from Sigma Corp. was also spotted onto the filters. The filters were then incubated for 45 minutes at room temperature with the detection solution, which consisted of 7 μl of an avidin coupled to horseradish peroxidase reagent (obtained commercially from Cappel Laboratories, Malvern, Pa.) per 10.0 ml of 1% bovine serum albumin (BSA) and 1× phosphate buffered saline (PBS) consisting of 0.15M NaCl and 0.0175M KH$_2$PO$_4$ brought to pH 7 with 0.01475M NaOH. Next the filters were washed three times for 5 minutes each with 0.5M NaCl, 0.01M H$_3$PO$_4$ of pH 6.5, 0.1% wt/vol BSA and 0.05% wt/vol Tween 20 surfactant. The filters were then washed three times for 5 minutes each with 0.3M NaCl and 0.03M sodium citrate at pH 7, 0.1% wt/vol BSA and 0.05% wt/vol Tween 20 surfactant. Then freshly prepared substrate solution, 0.5 mg/ml diaminobenzidine in 10 mM Tris-HCl pH 7.5 and 0.02% wt/vol H$_2$O$_2$, was added to the filters and kept in the dark for 15 minutes or more.

The product of the enzymatic reaction appeared as a precipitated stain. The DNA labeled with Compound XII was found to stain more darkly than DNA labeled with Compound II, whereas the DNA's labeled with Compound XII and with biotinylated uracil groups were roughly equal in staining intensity. These results indicate that Compound XII with a longer spacer arm of 18 atoms in the straight chain and an amide group when incorporated into DNA binds avidin to the same extent as the biotinylated uracil group when incorporated into DNA as taught by European Patent Publication No. 0,063,879.

In the next experiment, the ability of biopsoralenated DNA to hybridize specifically to filter-bound DNA and then be detected by avidin-horseradish peroxidase was tested. For this purpose the three biotin-labeled M13mp9CHL2.1 phage DNAs described above, which contained single-stranded 1.5 kilobase inserts homologous to pCHL2, were hybridized to filters spotted with the *Chlamydia trachomatis* clone pCHL2 and herring sperm DNA as follows: In this procedure, the plasmid DNA and sperm DNA were applied onto a filter, treated with 0.5N sodium hydroxide for 5 minutes to denature the DNA, and then neutralized by treating with a buffer consisting of 1M Tris-HCl and 1.5 M NaCl at pH 7. Thereafter, the filter was dried for 2 hours at 80° C. and treated with a prehybridization mixture of 0.2% wt/vol BSA, 0.2% wt/vol Ficoll, 0.2% wt/vol polyvinylpyrrolidone, a buffer of 0.9M NaCl, 0.05M sodium phosphate pH 7.0 and 0.005M EDTA, and 100 µg/ml of sheared and denatured herring sperm DNA, for about 2 hours. Then the filters were combined with a hybridization solution consisting of 50% wt/vol formamide, 10% wt/vol dextran sulfate, 0.2% wt/vol BSA, 0.2% wt/vol Ficoll, 0.2% wt/vol polyvinylpyrrolidone, a buffer of 0.9M NaCl, 0.05M sodium phosphate pH 7.0 and 0.005M EDTA, 100 µg/ml of sheared and denatured herring sperm DNA, and about 15 ng/ml of the respective DNA probes. This last hybridization step was carried out in a sealed plastic bag at 42° C. for 20 hours. After this time the samples were incubated with the detection solution of avidin and horseradish peroxidase and washed as described above, and then contacted with diaminobenzidine as described above to determine the amount of avidin binding. The results show that the M13 DNA probe labeled with Compound XII stained the darkest, although the probe labeled with Compound II stained almost as darkly. The comparative M13 DNA probe labeled with biotinylated uracil groups stained very poorly. The herring sperm negative control showed no stain. In these experiments the probes of this invention were able to detect 1 ng of the target 1.5 kilobase sequence easily.

These results indicate that the two biotinylated psoralen-labeled probes of this invention are superior in sensitivity to the probe labeled with biotinylated uracil nucleotide groups under these conditions. It is possible that the comparative compound is poorer because the strand labeled with the biotinylated nucleotides may dissociate and wash away under the stringent hybridization conditions. Thus, a potential important advantage of psoralen-crosslinked probes as compared to the M13 probe made by the Ward et al. modified nucleotide is that the region of the probe carrying the label will not dissociate from the probe under stringent hybridization conditions which are often necessary for distinguishing between closely related sequences.

To determine the sensitivity of the biopsoralenated probes of this invention, a second experiment was performed using the same hybridization conditions as described above except that 0.1 and 0.01 ng of the 1.5 kilobase pair target sequence contained in pCHL2 were spotted onto a filter and that hybridization was carried out for 40 hours rather than 20 hours. The 0.1 ng spot was visibly stained within 15 minutes, whereas the 0.01 ng spot was not visibly stained until several hours later for both biopsoralenated probes of this invention. The probe labeled with Compound XII was slightly superior to the probe labeled with Compound II.

B. Biotinylation of DNA Using Compounds XII (BP2) and XVI (BP3) and Hybridization to Chlamydia Using these Probes The two psoralen compounds were prepared using tritium labeled biotin in the reactions described previously. The source of DNA in this experiment was the M13 clone with the *Chlamydia trachomatis* insert, M13mp9CHL2.1 as described above. This single-stranded DNA was used as a template for partial second strand synthesis as described by Brown et al., *Gene*, 20, 193–194 (1982). One µg of the partially double-stranded M13 DNA was combined with 1500 pmoles of either of the two compounds in separate tubes in 1 µl TE (10 mM Tris-HCl pH 7, 0.1 mM EDTA). As a control, 1500 pmoles of either of the two compounds was combined with 1 µl TE in separate tubes. These tubes were irradiated with ultraviolet light at 360 nm at 30 mW/cm² for one hour. After irradiation, the reacted materials were spotted on TLC plates as described before. Incorporation was measured by using scintillation counting to determine the amounts of material in the different zones of the TLC plate. The result showed that Compound XVI incorporated into the DNA at a 30% higher level than Compound XII.

A dot blot hybridization experiment was performed to compare M13 probes labeled with the two compounds. The probes were the partially double-stranded M13 DNAs labeled in the previous experiment. The target DNA was the plasmid pCHL2 which contains a *Chlamydia trachomatis* insert. The target DNA and a control DNA obtained from herring sperm were applied and fixed to a Genetran membrane using the standard procedure of denaturation with 0.5M NaOH, followed by neutralization with 0.5M Tris-HCl pH 7, 3.0M NaCl, and fixation by baking at 80° C. for two hours in a vacuum oven. Prehybridizations of the membranes were done in 5× Denhardt's solution with 10% formamide, 5×SSPE, 0.5% SDS, 400 µg/ml tRNA for 16 hours at 45° C. The membranes were hybridized in 5× Denhardt's solution with 200 µg/ml sheared and denatured herring sperm DNA, 5×SSPE, 0.5% SDA, 50% formamide, and 2 ng/ml of either probe at 42° C. for 16 hours. The membranes were then washed three times at room temperature in 2×SSPE, 0.5% Tween 20 and three times at 60° C. in 0.26×SSPE, 0.5% Tween 20. Detection of the biotinyl groups on these probes was done using a Streptavidin-acid phosphatase complex commercially obtained from Enzo Biochemical using the detection procedures suggested by the manufacturer in its brochure. Hybridized probe was seen as a spot of precipitated stain due to the binding of the detection complex, and the subsequent reaction was catalyzed by acid phosphatase, which produced a precipitable dye.

The results indicated that the membrane hybridized to the probe labeled with Compound XVI had more intensely stained spots than did the membrane hybridized to the probe labeled with Compound XII. The higher sensitivity achieved with the probe labeled with Compound XVI was due to the higher incorporation of biotin label since the same amount of each probe was used. This experiment demonstrates the use and the advantage of Compound XVI in improving sensitivity in hybridization experiments.

EXAMPLE 9

Use of TMB to Visualize Nucleic Acid Hybridization on Genomic Southern Blots

I. Biotinylation of DNA Using Compounds XVI (BP3) and XXIII (BP6)

A probe for typing the human leukocyte antigen (HLA) system, designated as an HLA-DPα M13 hybridization probe, was prepared as follows:

A. Preparation of HLA-DRα Probe for Screening cDNA Library

An HLA-DRα probe was made to screen a cDNA library to identify a HLA-DPα clone as follows.

Four 11-mer oligonucleotides were prepared based on the known NH$_2$-terminal amino acid sequence (Glu, Phe, Tyr, Leu) of positions 11-14 of HLA-DRα antigen. The base sequences for the four oligonucleotides were as follows: (1) AGGTAAAATTC, (2) AGGTAGAATTC, (3) AGGTAAAACTC, and (4) AGGTAGAACTC. These sequences are all complementary to the codons for the indicated peptide sequence and were chosen to minimize degeneracy. The ambiguities are located at sequences positions 2, 3, 6, and 9. A G at positions 2 and 3 was chosen to minimize the destabilizing effect of potential mismatched base (G is capable of forming a wobble pair with U).

Because the four oligonucleotides were complementary to codons for amino acids 11-14, oligonucleotide primed cDNA synthesis on HLA-DRα mRNA was expected to generate a product of about 150–200 nucleotides. This estimate was based on a leader sequence of 75 nucleotides and assumes a 5' untranslated region of 75–125 nucleotides.

The specificities of the four 11-mers were compared by using them individually as primers in cDNA synthesis reactions using membrane-bound B cell mRNA, free B cell mRNA, and T cell mRNA as template. Only the AGGTAGAACTC oligonucleotide primed a cDNA band of 175 nucleotides which was enriched in reactions on B cell membrane-bound mRNA template. The specificity of this 11-mer oligonucleotide was confirmed by extending the primer in a cDNA synthesis reaction in the presence of a single dideoxy triphosphate and three deoxy triphosphates, an approach which has proved successful in the isolation of the HLA-B7 cDNA clone (Sood, et al, PNAS (1981) 78: 616–620). In the presence of dideoxy dATP, a minor cDNA band corresponding to a predicted 18-nucleotide primer extension product was observed. The additional seven nucleotides were determined by the wandering spot sequencing technique to be GGCCTGA. The following two additional nucleotides, AT, were inferred from the Ile codon, giving a nine nucleotide sequence that corresponded to the HLA-DRα antigen amino acids at positions 8, 9, and 10.

A 20-nucleotide fragment having the above determined sequence (AGGTAGAACTCGGCCTGAAT) was then synthesized by the triester method. The specificity of the 20-mer as a primer was examined in a cDNA synthesis reaction of poly(A+) mRNA from a B cell line. A major cDNA band, 175 nucleotides long, was synthesized; the nucleotide sequence of the eluted band corresponding to the expected sequence for HLA-DRα.

The specificity of the 20-nucleotide fragment as a hybridization probe was analyzed on a Northern blot of poly(A+)·mRNA. A unique band, at 1200–1300 nucleotides, resulted from probing B cell mRNA, but not T cell mRNA, with the $^{32}$P-labeled 20-mer nucleotide probe. Membrane-bound mRNA was enriched for the mRNA which hybridized to the 20-nucleotide probe.

An HLA-DRα cDNA clone was identified in a cDNA library with the above described 20-mer probe as follows. Membrane-bound RNA and free RNA were prepared, using phenol-chloroform extraction in the presence of Vanadyl complexes, from the human lymphoblastoid B cell line, CA. Poly(A+) mRNA, isolated by affinity chromatography with Poly U-Sepharose, was translated in an in vitro rabbit reticulocyte system. The partition of specific mRNA's into the membrane-bound and free fractions was monitored by 20D gel analysis of the $^{35}$S-labeled products of in vitro translation. A double-standed cDNA library was prepared from the membrane-bound mRNA using reverse transcriptase, DNA Polymerase I, and S1 nuclease. Following tailing with dCTP using terminal transferase, the cDNA was inserted and ligated to preparations of the plasmid pBR322 which had been digested with Pst and tailed with dGTP.

Initial screening of the library was carried out as follows. Duplicate sets ($\approx$4,000 clones/set) of Grunstein-Hogness colony filters were prepared. One set was probed with $^{32}$P cDNA made from size fractionated mRNA from the B cell line, CA. Sucrose gradient fractions were translated in an in vitro rabbit reticulocyte system and the $^{35}$S-labeled products analyzed by 20D gel electrophoresis to determine the appropriate fractions. The other set of filters was probed with $^{32}$P cDNA made from mRNA from the T cell line, Molt-4. A subset of about 150 clones, derived from membrane-bound, B cell specific, 12–14s mRNA, was defined by this initial screening.

Plasmid DNA was prepared from 25 pools, each consisting of 5 candidate cDNA clones and analyzed by dot hybridization with the $^{32}$P-labeled 20-nucleotide probe. Pool 14 plasmid DNA hybridized specifically with the probe. Subsequently, the individual members of the pool were tested; cDNA sequences complementary to the hybridization probe were restricted to the clone identified as 18C7.

In Northern blots, the $^{32}$P-labeled 18C7 nick translated probe hybridizes to a B cell mRNA of the same length (about 1200 to about 1300 nucleotides) as the band complementary to the 20-nucleotide probe. In genomic blots with DNA from a hamster-human hybrid containing the human chromosomes 6 and 3, the 18C7 probe hybridizes to a unique restriction fragment absent in the hamster parent, mapping the 18C7 DNA sequences to chromosome 6.

A more precise mapping was possible using the cell line 6.3.6 which has a small deletion at a defined site on the short arm of one homologue of the chromosome 6 pair. This deletion variant fails to express the HLA-A, B, C and HLA-DR specificities associated with one chromosome 6 halotype. In genomic blots 18C7 hybridizes to two restriction fragments from the parent cell line, presumably from the two chromosome 6's. Only one fragment is observed in DNA from the deletion variant; the other fragment is presumably derived from the chromosome which has been deleted. This result maps DNA sequences complementary to the 18C7 clone to the chromosomal site defined by the 6.3.6 deletion.

The human HLA-D locus is homologous to the mouse I region. In genomic blots with DNA from mouse congenic lines, inbred lines which differ only at the I region, the 18C7 probe hybridized to a restriction fragment that was different with each congenic line. This result maps DNA sequences complementary to the 18C7 clone to the mouse I region and therefore to the human HLA-D locus.

The 18C7 clone was confirmed as being HLA-DRα by analyzing its DNA sequence by the Maxam-Gilbert technique (*Methods in Enzymology* (1980) 65: 499–560) using the endonucleases PstI, HinfI, TaqI, Sau3A, AvaII, and BglI. The sequence for the coding strand of the HLA-DRα clone is given below.

done), 200 μg/ml sheared denatured salmon sperm DNA, at 37° C. for 24 hours with $1 \times 10^6$ cpm $^{32}$P-labeled. HLA-DRα probe ($2 \times 10^8$ cpm/μg, labeled by nick translation). Wash filters $3 \times 15$ minutes at room temperature in $5 \times$ SSPE, 0.1% SDS.

Under conditions of high stringency (wash at $0.1 \times$ SSPE, 65° C.), p29G8 hybridizes strongly only to itself. The coding strand of the p29G8 clone was sequenced using the Maxam-Gilbert procedure.

In genomic Southern blots, the p29G8 probe hybridizes to genomic restriction fragments distinct from those which hybridize to the HLA-DRα probe in DNA from an HLA hemizygous cell line (6.3.6). The genomic blot pattern with DNA from the cell line T5-1 and its HLA hemizygous derivative 6.3.6 indicates that the p29G8 locus maps within the HLA region. Comparison of the amino acid sequence encoded by this clone with

| | | | | |
|---|---|---|---|---|
| ATCATAGCTG | TGCTGATGAG | CGCTCAGGAA | TCATGGGCTA | TCAAAGAAGA |
| ACATGTGATC | ATCCAGGCCG | AGTTCTATCT | GAATCCTGAC | CAATCAGGCG |
| AGTTTATGTT | TGACTTTGAT | GGTGATGAGA | TTTTCCATGT | GGATATGGCA |
| AAGAAGGAGA | CGGTCTGGCG | GCTTGAAGAA | TTTGGACGAT | TTGCCAGCTT |
| TGAGGCTCAA | GGTGCATTGG | CCAACATAGC | TGTGGACAAA | GCCAACCTGG |
| AAATCATGAC | AAAGCGCTCC | AACTATACTC | CGATCACCAA | TGTACCTCCA |
| GAGGTAACTG | TGCTCACGAA | CAGCCCTGTG | GAACTGAGAG | AGCCCAACGT |
| CCTCATCTGT | TTCATCGACA | AGTTCACCCC | ACCAGTGGTC | AATGTCACGT |
| GGCTTCGAAA | TGGAAAACCT | GTCACCACAG | GAGTGTCAGA | GACAGTCTTC |
| CTGCCCAGGG | AAGACCACCT | TTTCCGCAAG | TTCCACTATC | TCCCCTTCCT |
| GCCCTCAACT | GAGGACGTTT | ACGACTGCAG | GGTGGAGCAC | TGAGGCTTGG |
| ATGAGCCTCT | TCTCAAGCAC | TGGGAGTTTG | ATGCTCCAAG | CCCTCTCCCA |
| GAGACTACAG | AGAACGTGGT | GTGTGCCCTG | GGCCTGACTG | TGGGTCTGGT |
| GGGCATCATT | ATTGGGACCA | TCTTCATCAT | CAAGGGAGTG | CGCAAAAGCA |
| ATGCAGCAGA | ACGCAGGGGG | CCTCTGTAAG | GCACATGGAG | GTGATGATGT |
| TTCTTAGAGA | GAAGATCACT | GAAGAACTT | CTGCTTTAAT | GACTTTACAA |
| AGCTGGCAAT | ATTACAATCC | TTGACCTCAG | TGAAAGCAGT | CATCTTCAGC |
| GTTTTCCAGC | CCTATAGCCA | CCCCAAGTGT | GGTTATGCCT | CCTCGATTGC |
| TCCGTACTCT | AACATCTAGC | TGGCTTCCCT | GTCTATTGCC | TTTTCCTGTA |
| TCTATTTTCC | TCTATTTCCT | ATCATTTTAT | TATCACCATG | CAATGCCTCT |
| GGAATAAAAC | ATACAGGAGT | CTGTCTCTGC | TATGGAATGC | CCCATGGGGC |
| TCTCTTGTGT | ACTTATTGTT | TAAGGTTTCC | TCAAACTGTG | ATTTTTCTG |

A $^{32}$P-labeled HLA-DRα probe was made from the clone by nick translation.

B. Preparation of Hybridization Probes for HLA-DPα (Using Clones p29G8 and pDA318)

A HLA-DPα clone, p29G8, was identified by screening the cDNA library described above with the nick-translated HLA-DRα probe under hybridization conditions of reduced stringency to allow detection of related but distinct DNA sequences. The hybridization conditions were as follows.

Hybridize in 50% formamide, $5 \times$ SSPE ($1 \times$ SSPE=0.18M NaCl, 10 mM NaH$_2$PO$_4$, 1 mM Na$_2$EDTA, pH 7.0), 0.1% sodium dodecyl sulfate (SDS), $5 \times$ Denhardt's ($5 \times$ Denhardt's=0.1% w/v each bovine serum albumin, Ficoll, polyvinyl pyrollipublished amino acid sequence data for HLA-DPα antigen indicated that p29G8 is an HLA-DPα clone. A $^{32}$P-labeled probe was made from the clone by nick translation.

The p29G8 probe was hybridized to another cDNA library made with EcoRI linking. The DP-α cDNA sequence was subcloned into the EcoRI site of pBR328, which is commercially available from Boehringer-Mannheim, and is a relative of pBR322, to produce the plasmid, pDA318, which was deposited in an MM294 host with the American Type Culture Collection under accession no. 39,917 on Nov. 8, 1984. The plasmid pDA318 is larger than p29G8 and includes the p29G8 sequence. The sequence of the cDNA insert in pDA318 is given below.

```
AGTCTCATCTGCCTCCACTCGGCCTCAGTTCCTCATCACTGTTCCTGTGCTCACAGTCAT
CAATTATAGACCCCACAACATGCGCCTGAAGACAGAATGTTCCATATCAGAGCTGTGAT
CTTGAGAGCCCTCTCCTTGGCTTTCCTGCTGAGTCTCCGAGGAGCTGGGGCCATCAAGGC
GGACCATGTGTCAACTTATGCCGCGTTTGTACAGACGCATAGACCAACAGGGGAGTTTAT
GTTTGAATTTGATGAAGATGAGATGTTCTATGTGGATCTGGACAAGAAGGAGACCGTCTG
GCATCTGGAGGAGTTTGGCCAAGCCTTTTCCTTTGAGGCTCAGGGCGGGCTGGCTAACAT
TGCTATATTGAACAACAACTTGAATACCTTGATCCAGCGTTCCAACCACACTCAGGCCAC
CAACGATCCCCCTGAGGTGACCGTGTTTCCCAAGGAGCCTGTGGAGCTGGGCCAGCCCAA
CACCCTCATCTGCCACATTGACAAGTTCTTCCCACCAGTGCTCAACGTCACGTGGCTGTG
CAACGGGGAGCTGGTCACTGAGGGTGTCGAGGAGCCTCTTCCTGCCCAGAACAGATTA
CAGCTTCCACAAGTTCCATTACCTGACCTTTGTGCCCTCAGCAGAGGACTTCTATGACTG
CAGGGTGGAGCACTGGGGCTTGGACCAGCCGCTCCTCAAGCACTGGGAGGCCCAAGAGCC
AATCCAGACGCCTGAGACAACGGAGACTGTGCTCTGTGCCCTGGGCCTGGTGCTGGGCCT
AGTCGGCATCATCGTGGCGGCACCGTCCTCATCATAAAGTCTCTGCGTTCTGGCCATGACCC
CCGGGCCCAGGGGACCCTGTGAAATACTGTAAAGGTGACAAAATATCTGAACAGAAGAGG
ACTTAGGAGAGATCTGAACCAGCTGCCCTACAAACTCCATCTCAGCTTTTCTTCTCACTT
```

-continued

```
CATGTGAAAACTACTCCAGTGGCTGACTGAATTGCTGACCCTTCAAGCTCTGTCCTTATC
CATTACCTCAAAGCAGTCATTCCTTAGTAAAGTTTCCAACAAATAGAAATTAATGACACT
TTGGTAGCACTAATATGGAGATTATCCTTTCATTGAGCCTTTTATCCTCTGTTCTCCTTT
GAAGAGCCCCTCACTGTCACCTTCCCGAGAATACCCTAAGACCAATAAATACTTCAGTAT
T
```

The phage strain M13mp10 (commercially available from Boehringer-Mannheim and described on pages 88–89 of the 1983 BRL Catalog) was employed. The M13mp10 is essentially the same as M13mp9 except for its cloning region, which is provided in FIG. 3B. FIG. 3 provides the differences between these regions of M13mp9 and M13mp10. Both the cDNA insert of pDA318 and M13mp10 R.F. DNA were cut with EcoRI restriction enzyme and then the DNA fragments were ligated together and used to transform the *E. coli* strain JM103, which is publicly available from Bethesda Research Laboratories in Bethesda, Md. The procedure followed for preparing the transformed strain is described in Messing, J. (1981) *Third Cleveland Symposium on Macromolecules: Recombinant DNA*, Ed. A. Walton, Elsevier, Amsterdam, 143–153. Restriction analysis established that one of the single-stranded M13 candidates excreted into the medium contained the desired pDA318 1200 base insert in the desired orientation. M13 phage containing the 1200 base insert were isolated and the DNA was purified by treatment with phenol.

A double-stranded form of M13 DNA was obtained from M13-infected cells as described by Van den Hondel et al., (1976) *Eur. J. Biochem.* 68: 55–70. This double-stranded DNA was linearized with a suitable restriction enzyme.

Using this linearized double-stranded M13 DNA and the single strand above, the following procedure was employed to obtain double-stranded circular DNA probes with a single-stranded "gap" containing the HLA DP-α insert as described by Courage-Tebbe et al., (1982), *Biochem. Biophys. Acta*, 697: 1–5. The linearized double-stranded M13 DNA, in the presence of a molar excess of the viral single-stranded circular M13 DNA containing the cloned insert, was denatured by addition of base, partially neutralized and allowed to renature, neutralized by addition of acid, and then chromatographed on hydroxyapatite.

A DQα cDNA clone was prepared as described in copending U.S. patent application Ser. No. 678,255 filed Dec. 5, 1984 to H. Erlich and inserted into a circular M13 DNA probe as described above for the DPα insert.

The DNA removed from the column was a partially double-stranded gapped circle DNA probe, with the hybridizing region representing the single-stranded portion. The DPα and DQα probes were labeled separately with Compound XVI (BP3) or Compound XXIII (BP6) by combining one μg of each probe with 420 pmoles of Compound XVI or 2,100 pmoles of Compound XXIII. The tubes were irradiated with ultraviolet light at 360 nm at 30 mW/cm$^2$ and the reacted materials were isolated.

Biotinylated molecular weight markers for identifying the bands seen on Southern blots were made from bacteriophage Lambda DNA which had been digested to completion with the restriction endonuclease, BstEII (supplied by New England Biolabs), and biotinylated with Compound XVI in the manner just described for labeling a DNA probe.

II. Hybridization of Probes to HLA Insert

Two μg of human DNA were digested with the restriction endonuclease BglII, electrophoresed through 1% agarose minigels, and transferred to one of three nylon membranes (Genatran 45 of Plasco Inc., Zeta-Probe of BioRad, or Zetabind of AMF Cuno), using the method as described by Southern ((1975) JMB 98: 503–517). Other nylon membranes have not worked as well. In some lanes biotinylated DNA molecular weight markers (described above) or a positive control consisting of genomic DNA isolated from a homozygous typing cell line WT51 (Tissue Antigen Laboratory, Imperial Cancer Research Fund, London, England) was included. After transfer to the membrane the filter-bound human DNA was fixed on the membrane using the standard procedure with base, neutralization with Tris-HCl buffer and baking at one hour or longer at 80° C. in a vacuum oven, as described by Southern, supra. The membrane was then wetted with distilled water for one minute, and placed in a sealable pouch. A prehybridization solution was then added to the membrane consisting of 2.4×—5×Denhardt's solution with 22% formamide, 5×SSPE, 0.5% (w/v) SDS, and 150 μg/ml denatured herring sperm DNA (available from Sigma). The membrane was incubated with the solution for 2–4 hours at 42°–45° C. Then a hybridization solution was added to the membrane in an amount of 0.1 ml solution/cm$^2$ membrane consisting of 5×Denhardt's solution with 150 μg/ml denatured herring sperm DNA (sheared before denaturation by repeated passage through a 25 gauge hypodermic needle to reduce viscosity, if necessary for hybridization), 5×SSPE, 0.5% (w/v) SDS, 5–10% dextran sulfate, 50% formamide, and 50–200 ng per ml of either probe and the membrane was incubated overnight (about 14–18 hours) at about 42° C. The membrane was then washed three times for five minutes each with shaking at room temperature in 2×SSPE, 0.5% Tween 20 and three times at 60° C. for five minutes with shaking in 0.26×SSPE, 0.5% Tween 20.

III. Horseradish Peroxidase-Streptavidin (HRP-SA) Conjugate Preparation

Horseradish peroxidase (HRP) quantities were calculated from an assumed molecular weight of 40,000 g/mole and an assumed $A_{402, 1\,cm, 0.1\%}$ of 2.5. Streptavidin (SA) quantities were calculated from an assumed molecular weight of 60,000 g/mole and an assumed $A_{280, 1\,cm, 0.1\%}$ of 3.0.

To 40 mg of HRP (Sigma Chemical Co. Type VI), dissolved in 1.9 ml of 0.10M Na phosphate, pH 7.5, and dialyzed at 4° C. against the same buffer, were added 0.14 ml of 14 mg/ml mal-sac-HNSA ester dissolved in the same buffer. [mal-sac-HNSA ester is the subject of copending patent application Ser. No. 637,905 filed Aug. 6, 1984 and is also described by Bhatnagar et al., *Peptides: Synthesis-Structure-Function*, ed. by D. Rich et al. (Rockford: Pierce Chemical Company, 1981), p. 97 where the preparation of mal-sac-HNSA ester parallels that of DNP-SAC and TNP-SAC esters using as the acid N-maleimido-6-aminocaproic acid.] This mixture was incubated for 105 min at room temperature, desalted on a 9 ml column of Sephadex G-25 equilibrated with 0.010M Na phosphate, 0.005M EDTA, pH 6.0, and dialyzed at 4° C. against three 200 ml volumes of the same buffer. The maleimide content of the derivatized HRP was assayed by diluting 0.2 mg in 0.50 ml 0.10M Na phosphate, 0.005M EDTA, pH 7.0, adding 20 $\mu$l of 0.74 mM cysteine, incubating 5 min at room temperature, adding 33 $\mu$l of 4 mg/ml 5,5'-dithiobis(2-nitrobenzoic acid), incubating 2 min at room temperature, and measuring $A_{412}$ in a spectrophotometer. The difference in $\Delta A_{412}$ between this reaction and one for a control mixture to which no protein had been added, divided by the $\Delta \epsilon_{412}$ of $1.36 \times 10^4 M^{-1} cm^{-1}$, gave the molarity of maleimide in the diluted HRP.

Fifteen mg of SA (Sigma Chemical Co.) were dissolved in 1.5 ml of 0.10M Na phosphate, pH 8.0, dialyzed at 4° C. against three 200 ml volumes of the same buffer, and diluted to a concentration of 6 mg/ml in the same buffer. S-acetyl mercaptosuccinic acid (SAMCA, Aldrich Chemical Co.) was dissolved in dimethyl formamide at a concentration of 8.8 mg/ml. To 12 mg of dialyzed SA were added 125 $\mu$l of this SAMCA solution with gentle stirring at room temperature over about 1 min. After 30 min incubation at room temperature, the reaction mixture was desalted on a 9 ml column of Sephadex G-25 equilibrated with 0.10M TrisCl, 0.005M EDTA, pH 6.8. The pooled protein was dialyzed at 4° C. against three 200 ml volumes of the same buffer. The dialyzed derivatized SA was concentrated at room temperature to 10 mg/ml in an Amicon 8 MC ultrafiltration device with a YM10 membrane. Ten mg of concentrated SA were mixed with 0.5 ml of 1.0M hydroxylamine in 1.10M TrisCl, 0.005M EDTA, pH 6.8 with gentle stirring. After a 30 min incubation at room temperature, the SA was desalted on a 9 ml column of Sephadex G-25 equilibrated with 0.010M Na phosphate, 0.005M EDTA, pH 6.0. A small aliquot of the pooled protein peak was assayed for reactive thiols by measuring the change in $A_{412}$ after adding 5,5'-dithiobis(2-nitrobenzoic acid) to a concentration of 1 mM in 0.10M Na phosphate, pH 8.0.

The assays of maleimide on HRP and of thiols on SA were done immediately before mixing them to perform the coupling reaction. The 3.95 ml of 13.0 mg/ml HRP bearing 0.67 maleimides/HRP were mixed in an ice bath with 2.47 ml of 4.19 mg/ml SA bearing 9.66 thiols/SA. After a 24 hr incubation at 5 C., the unreacted thiols were blocked by adding 0.47 ml of 4.6 mg/ml N-ethyl maleimide dissolved in acetonitrile and incubating at room temperature for 30 min.

The reaction mixture was fractionated into conjugate pools of different mean HRP/SA molar ratio, separated from unreacted HRP by gel filtration chromatography on a 2.5×80 cm column of Ultrogel AcA 44 (LKB Instruments) at 4 C. in 0.10M Na phosphate, pH 6.8, at a flow rate of 3 cm/hr. The composition of the conjugate pools was estimated spectrophotometrically from the $A_{402}/A_{280}$ ratio and quantitated accurately by densitometric scanning of a Nuclear Fast Green stained 6–20% gradient SDS-PAGE gel, run under reducing conditions. Approximately 10 mg of mixed 2-mer and 3-mer (species containing 2 HRP:SA and 3 HRP:SA) and 5 mg of fairly pure 1-mer were recovered from gel filtration. These conjugate pools, containing no detectable uncoupled SA or HRP, were stored at 4° C. for many months with negligible loss of protein or HRP catalytic activity. The mixture of 2-mer and 3-mer was used preferentially in detecting biotinylated DNA probe hybridized to human genomic Southern blots, but 1-mer gave almost the same intensity of staining.

IV. Probe Detection

All operations took place at room temperature. The probehybridized Southern blot from Section IB of this example was rinsed once in 35 ml of phosphate-buffered saline to which had been added 0.1M NaCl and 5% Triton X-100 (Buffer A). After 5 min of gentle agitation in a plastic Petri dish, the rinse solvent was replaced with 10 ml of Buffer A containing HRP-SA at a concentration such that the component HRP was present at 0.3 $\mu$g/ml. Conjugate was incubated with the blot for 20 min without agitation. Then the blot was removed at a clean Petri dish and rinsed 5 times with 45 ml volumes of Buffer A to which had been added 0.15M 1,1-diethylurea. These 5 minute washes with gentle agitation were followed by one 5 minute wash with gentle agitation in 45 ml of 0.10M Na citrate, 5% ethanol, pH 5.0, (Buffer C) containing 0.1 mg/ml TMB. At this point, the blot was incubated undisturbed in 50 ml of Buffer C containing 0.1 mg/ml TMB and 0.0007% $H_2O_2$. Over 15–60 minutes, dark blue bands developed on the blot wherever biotinylated DNA was located—either biotinylated DNA fragments in the molecular weight standards or biotinylated probe hybridized to targeted DNA. When satisfactory contrast was obtained by peroxidative staining, the substrate solution was drained from the blot, which was rinsed once for 30-60 min in 50 ml Buffer C with gentle agitation. The washed membrane was stored in 0.10M Na citrate, pH 5.0, in a sealed test tube or plastic bag in the dark at 4° C. or −20° C.

When 2 $\mu$g of DNA from a human subject bearing the DQ$\alpha$ HLA gene were subjected to the analysis just described, and the Southern blot was hybridized with a circular DNA probe containing a DQ$\alpha$ insert and covalently tagged with 0.05 moles of Compound XVI per mole of DNA base pair, the pattern obtained after HRP-TMB visualization contained two bands of equal intensity, one at 2.3 kilobases and one at 4.7 kilobases, relative to biotinylated moleculear weight standards on the same blot.

EXAMPLE 10

Incorporation of Compound III Into DNA and Detection of Resulting Probe

Compound III containing a fluorescein molecule was incubated with double-stranded sheared herring sperm DNA at 25° C. for 20 minutes and then irradiated with a UV light at 360 nm for 1.5 hours. The result was that the DNA had incorporated Compound III as determined by electrophoresis through a 1% agarose gel and by subsequent detection of the green fluorescence of Compound III, when exposed to short-wave ultraviolet light, at the same position as the DNA. Because compound III has a net positive charge, normally it would not comigrate with DNA.

Compound III is also expected to have use as a method for staining or banding specific regions of chromosomes using generally the procedure described by V. G. Dev et al., *Lancet* (England), 1, 1285 (June 10, 1972). Thus, specific chromosomes can be recognized and counted.

It is expected that this probe can also be used to detect nucleic acid sequences under the hybridization conditions as described above and can be detected by fluorescent light.

It is noted that the M13 gapped circle method for obtaining nucleic acids where a double-stranded region is adjacent to a single-stranded hybridization region does not involve the use of relatively expensive enzymes such as DNA polymerase I which are required in the methods of incorporating biotin into DNA taught by, e.g., Leary et al., supra, and EP No. 0,063,879 to Ward, supra.

The deposit identified as the plasmid pDPα-318 in a MM294 host was deposited with the American Type Culture Collection (ATCC) of Rockville, MD 20852 USA under accession no. 39,917 on Nov. 8, 1984 pursuant to a contrast between the ATCC and the assignee of this patent application, Cetus Corporation. The contract with ATCC provides for permanent availability of the progeny of this plasmid-containing host to the public on the issuance of the U.S. patent describing and identifying the deposit or the publications or upon the laying open to the public of any U.S. or foreign patent application, whichever comes first, and for availability of the progeny of this host to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the host on deposit should die or be lost or destroyed when cultivated under suitable conditions, it will be promptly replaced on notification with a viable culture of the same host.

In summary, the present invention is seen to provide a detectable probe which may be used in hybridization to detect the presence of nucleic acid sequences in samples suspected of containing the same. In addition, the invention provides processes for making the probe and for detecting nucleic acids in test samples.

Those skilled in the art should note that the disclosure herein on particular embodiments of the present invention is exemplary only, and that various other alternatives, adaptations, and modifications may be made within the scope of the present invention. Accordingly, the present invention is not limited to the specific embodiments as illustrated herein, and is embodied in the claims appended hereto.

What is claimed is:

1. A compound of the formula:

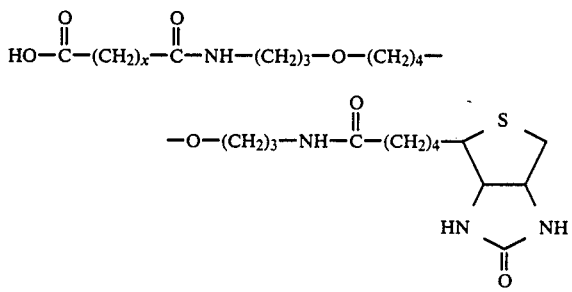

wherein x is 2 or 3.

2. The compound of claim 1 wherein x is 2.

* * * * *